United States Patent
Wang et al.

(10) Patent No.: US 10,119,891 B2
(45) Date of Patent: Nov. 6, 2018

(54) TRACEABLE EMISSION REMOTE MONITORING SYSTEM AND METHOD

(71) Applicant: TECTICOM ENVIRONMENTAL TECHNOLOGY LIMITED, Hong Kong (CN)

(72) Inventors: Yingfeng Wang, Hong Kong (CN); Hao Li, Hubei (CN); John Jianhua Liu, Hong Kong (CN); Jim S. Liu, Los Angeles, CA (US)

(73) Assignee: TECTICOM ENVIRONMENTAL TECHNOLOGY LIMITED, Hong Kong (CN)

( * ) Notice: Subject to any disclaimer, the term of this patent is extended or adjusted under 35 U.S.C. 154(b) by 71 days.

(21) Appl. No.: 15/127,257

(22) PCT Filed: Oct. 14, 2015

(86) PCT No.: PCT/CN2015/091903
§ 371 (c)(1),
(2) Date: Sep. 19, 2016

(87) PCT Pub. No.: WO2016/062216
PCT Pub. Date: Apr. 28, 2016

(65) Prior Publication Data
US 2017/0350795 A1 Dec. 7, 2017

(30) Foreign Application Priority Data

Oct. 22, 2014 (CN) .......................... 2014 1 0563080

(51) Int. Cl.
*G01N 1/22* (2006.01)
*G07C 5/00* (2006.01)
(Continued)

(52) U.S. Cl.
CPC .......... *G01N 1/2273* (2013.01); *G01F 15/061* (2013.01); *G05B 19/4188* (2013.01); *G07C 5/008* (2013.01); *G01N 2001/021* (2013.01)

(58) Field of Classification Search
CPC ................ G01N 1/2273; G01F 15/061; G05B 19/4188; G07C 5/008
See application file for complete search history.

(56) References Cited

U.S. PATENT DOCUMENTS

| 5,767,790 A | 6/1998 | Jovellana | |
|---|---|---|---|
| 2008/0167772 A1* | 7/2008 | Du .......................... | G07C 5/008 701/31.4 |
| 2016/0018373 A1* | 1/2016 | Page ..................... | G01N 1/2273 436/55 |

FOREIGN PATENT DOCUMENTS

| CN | 1936995 A | * | 3/2007 |
|---|---|---|---|
| CN | 102419584 A | | 4/2012 |

(Continued)

OTHER PUBLICATIONS

Machine Translation of CN1936995A.*
Written Opinion and International Search Report for International Application No. PCT/CN2015/091903 dated Jan. 1, 2016 (8 pages).

*Primary Examiner* — Nabil Syed
(74) *Attorney, Agent, or Firm* — Fitch Even Tabin & Flannery, LLP

(57) ABSTRACT

The present invention discloses a Traceable emission remote monitoring system and method. The system comprises a remote sensing unit, a transformation data processor, and a local control unit. The local control unit receives local resource information to generate control commands and transmits the same to the remote sensing unit; the remote sensing unit remotely senses emissions that an object emits based on the control commands, and transmits individual emission data to the transformation data processor for processing and analysis to obtain a first analytic result; the local (Continued)

control unit provides various derivative services to generate a second analytic result. In some embodiments, the system further comprises a cloud platform for generating a comprehensive analysis report. The present invention further discloses a traceable emission remote sensing method. The Traceable emission remote monitoring system and method according to the present invention are real-time, convenient, fast and accurate, and can make it digitalized and networked for the emissions that a single object emits and the emission of regional and trans-regional comprehensive emissions, and can thus help the supervision department formulate effective regulatory strategies.

16 Claims, 5 Drawing Sheets

(51) Int. Cl.
    *G01F 15/06*      (2006.01)
    *G05B 19/418*      (2006.01)
    *G01N 1/02*      (2006.01)

(56) References Cited

FOREIGN PATENT DOCUMENTS

| | | | |
|---|---|---|---|
| CN | 102685201 A | | 9/2012 |
| CN | 102778537 A | | 11/2012 |
| CN | 102830674 A | * | 12/2012 |
| CN | 102968097 A | | 3/2013 |

* cited by examiner

Traceable Emission Remote-Sensing System 100

Traceable Emission Remote-Sensing System 100

Local Resource Information

TRACEABLE EMISSION REMOTE MONITORING SYSTEM AND METHOD

CROSS-REFERENCE TO RELATED APPLICATION

This application is a U.S. national phase application of International Application No. PCT/CN2015/091903, filed Oct. 14, 2015, designating the United States, which claims priority to Chinese Application No. 201410563080.1, filed Oct. 22, 2014, both of which are incorporated by reference herein in their entirety.

TECHNICAL FIELD

The present invention generally relates to the field of emissions and, in particular, the present invention relates to a traceable emission remote monitoring system and method.

BACKGROUND

Mobile emission emitting objects, such as vehicles, ships, and aircrafts, and non-mobile emission emitting objects, such as chimneys of factories like power plants, oil refineries and so on often release harmful gases, such as oxysulfides, oxynitrides, carbon monoxides and hydrocarbons, etc, thereby causing haze, greenhouse effect, acid rain and/or damage to the atmospheric ozone layer, and endangering the global environment and human health. Therefore, it is necessary to trace and monitor the emissions that the objects emit, in particular, in populous cities.

At present, sampling technology is usually adopted in emission monitoring and detection, carried out mainly by professional staff at stationary monitoring stations or directly near the emitting objects. It also begins to come into existence that a detection device and an analysis device are arranged inside the emitting objects for continuous detection. However, on-board tracing and detection have not yet taken shape owing to the problems of technology, cost and the like. For example, according to the provision of the International Maritime Organization, when a ship approaches a port or a dock, a fuel used during an ocean-going voyage is required to be replaced with a fuel having a much lower sulfur content, and the sulfur contents between the two fuels generally differ for ten times or so. If the provision is to be executed, it is required to detect a single ship when the ship approaches the port or dock. According to the detection technology that can be provided currently, a method of boarding sampling detection is mainly adopted. A random inspection method is usually adopted due to the problems of cost and technology of boarding detection, and it is required that each of the docked shipowners should regularly submit bills and documents of the fuels used instead for confirming evaluation and serving as the major basis for random inspection. Such detection method is not only inconvenient and time- and cost-consuming, but also cannot realize real-time detection. Moreover, it is also possible that the shipowners will bribe the inspectors in order not to change for more expensive, high quality fuels, thereby providing false detection reports. Besides, the prior art detection methods are only limited to non-network type analytic calculation and physical detection, and cannot efficiently realize sharing of the individual emission information in a wider range. Furthermore, for example, in accordance with the Hong Kong Shipping and Port Regulations, penalties should be applied to black smoke emission that exceeds certain blackness, which are accomplished at present generally in a way that the supervisors identify and compare color cards through human eyes. However, such method is time- and labor-consuming and subjective, hence is not suitable for long-term tracing and detection of all the ships.

Therefore, it is very necessary to develop a new detection system and method, thereby efficiently tracing and detecting emissions that an object emits.

SUMMARY OF THE INVENTION

With respect to the foregoing defects in the detection of emissions that the objects emit in the prior art, the present invention provides a new traceable emission remote monitoring system and method.

According to one aspect of the present invention, the present invention provides a Traceable Emission Remote Monitoring System.

According to a preferred embodiment of the present invention, the system comprises: a remote sensing unit for manipulating remote sensing of emissions that an object emits and collecting individual emission data of the emitting objects via remote sensing technology; a transformation data processor connected to the remote sensing unit by viable telecommunication means, for receiving the individual emission data and analyzing the individual emission data to obtain a first analytic result; and a local control unit respectively connected to the remote sensing unit and the transformation data processor, for receiving local resource information and generating control commands for manipulating remote sensing of the emissions that the object emits based on the local resource information, and receiving the first analytic result from the transformation data processor, and analyzing the first analytic result and/or a second analytic result previously stored in the local control unit to obtain a new second analytic result, and storing the new second analytic result.

According to a preferred embodiment of the present invention, the system further comprises: a cloud platform connected to the local control unit by viable telecommunication means, the cloud platform being used for receiving and storing the new second analytic result from the local control unit, and comprehensively analyzing the new second analytic result and/or all or part of the second analytic result previously stored in the cloud platform to obtain a comprehensive analysis report.

According to a preferred embodiment of the present invention, the remote sensing unit comprises: a remote sensing device for collecting individual emission data of an object that emits emissions via remote sensing technology; and an embedded module connected to the remote sensing means, the embedded module being used for receiving from the local control unit control commands for manipulating remote sensing of the emissions that the object emits and manipulating the remote sensing of the emissions that the object emits based on the control commands, and receiving the individual emission data from the remote sensing means, and transmitting the individual emission data to the transformation data processor for processing.

According to a preferred embodiment of the present invention, the transformation data processor comprises a spectral signal processing module for analyzing the individual emission data to obtain a first analytic result.

According to a preferred embodiment of the present invention, the transformation data processor further comprises a spectrum signal buffering module connected to the spectral signal processing module, for receiving individual emission data collected from the remote sensing unit, and buffering the individual emission data and transmitting the same to the spectral signal processing module for processing.

According to a preferred embodiment of the present invention, the transformation data processor further comprises an auxiliary information module connected to the spectral signal processing module for storing auxiliary information which comprises one or more of an existing spectral library, position of an emitting object, ambient temperature, wind speed and humidity, and the spectral signal processing module analyzes the individual emission data in combination with the auxiliary information to obtain a first analytic result.

According to a preferred embodiment of the present invention, the local control unit comprises: a scheduling module for receiving local resource information; a control module connected to the scheduling module, for receiving local resource information from the scheduling module, and generating control commands for manipulating remote sensing of emissions that an object emits based on the local resource information; an emission derivative service module for analyzing the first analytic result and/or a second analytic result previously stored in the local control unit to obtain a new second analytic result; and a local storage module for receiving and storing the first analytic result from the transformation data processor and receiving and storing the new second analytic result from the emission derivative service module.

According to a preferred embodiment of the present invention, the cloud platform comprises: a storage module for receiving and storing the new second analytic result from the local control unit; a comprehensive service module for comprehensively analyzing the new second analytic result and/or all or part of the second analytic result previously stored in the storage module to obtain a comprehensive analysis report, wherein the obtained comprehensive analysis report is stored in the storage module; and a user I/O interface via which a user is allowed to interact with the cloud platform.

According to a preferred embodiment of the present invention, the remote sensing unit is further used for transmitting feedback information to the local control unit, and the local control unit is further used for responding to the feedback information, wherein the feedback information comprises one or both of status feedback information and fault feedback information of the remote sensing unit, and the responding comprises the local control unit generating new control commands according to the feedback information, and transmitting the new control commands to the remote sensing unit to instruct manipulation of remotely sensing emissions that the object emits.

According to a preferred embodiment of the present invention, the individual emission data are transmitted and stored in the local control unit, and the individual emission data and the first analytic result are further uploaded or synchronized to the cloud platform and stored therein.

According to another aspect of the present invention, the present invention provides a traceable emission remote sensing method.

According to a preferred embodiment of the present invention, the method comprises: receiving local resource information, and generating control commands for manipulating remote sensing of emissions that an object emits based on the local resource information; initiating remote sensing of the emissions that the object emits according to the control commands to collect individual emission data; analyzing the individual emission data to obtain a first analytic result, and transmitting the first analytic result to the local control unit; and analyzing the first analytic result and/or a second analytic result previously stored in the local control unit to obtain a new second analytic result and storing the new second analytic result in the local control unit.

According to a preferred embodiment of the present invention, the method further comprises uploading or synchronizing the new second analytic result to a cloud platform and storing the same in the cloud platform; and comprehensively analyzing the new second analytic result and/or all or part of the second analytic result previously stored in the cloud platform to obtain a comprehensive analysis report.

According to a preferred embodiment of the present invention, the method further comprises: transmitting feedback information to the local control unit; and the local control unit responding to the feedback information, wherein the feedback information comprises one or both of status feedback information and fault feedback information of the remote sensing unit, and the responding comprises the local control unit generating new control commands according to the feedback information, and transmitting the new control commands to the remote sensing unit to instruct manipulation of remotely sensing emissions that the object emits.

According to a preferred embodiment of the present invention, the method further comprises: analyzing the individual emission data in combination with auxiliary information to obtain the first analytic result, wherein the auxiliary information comprises one or more of a spectral library, position of an emitting object, ambient temperature, wind speed and humidity.

According to a preferred embodiment of the present invention, the method further comprises buffering the individual emission data prior to analyzing the same.

According to a preferred embodiment of the present invention, the method further comprises: transmitting and storing the individual emission data in a local control unit, and uploading or synchronizing the individual emission data and the first analytic result to a cloud platform and storing the same therein.

In comparison with the existing emission detection technology of the emitting objects, the technical solution provided by the present invention provides various advantages.

According to some embodiments of the present invention, the traceable emission remote monitoring system and method of the present invention may realize real-time continuous detection of emitting objects at multiple places simultaneously. Such non-sampling detection system and method is convenient and efficient, and will not disturb normal operation of the emitting objects at all.

According to some embodiments of the present invention, the Traceable emission remote monitoring system and method of the present invention may rapidly analyze the individual emission data collected in real time, rapidly determine whether the objects that emit the emissions have changed the fuels, and generate enterprise self-check reports required to be submitted according to the requirements of the supervision department or fill in corresponding data required in the self-check reports. The Traceable emission remote monitoring system and method not only is simple, fast, and efficient, but also satisfactorily eradicates the existing conditions that the enterprises provide false detection reports.

According to some embodiments of the present invention, the Traceable emission remote monitoring system and method of the present invention can rapidly and accurately detect the emissions that each of the objects emit, rather than merely roughly estimating the emissions that a certain category and/or a certain model of objects emit as in the prior art.

According to some embodiments of the present invention, the Traceable emission remote monitoring system and method of the present invention can further take into account auxiliary information such as ambient temperature, wind speed, humidity and the like, and thereby can analyze the emissions that the objects emit in a more accurate manner.

According to some embodiments of the present invention, the Traceable emission remote monitoring system and method of the present invention can further realize emission digitization of a single object that emits emissions, and the digital information concerning the emissions that the single object emits may be shared in a wider range or even worldwide via a cloud platform, thereby significantly facilitating supervision of the emission. For example, purposeful supervision and service may be carried out on the single object that emits emissions and a specific type of emitting objects.

According to some embodiments of the present invention, the Traceable emission remote monitoring system and method of the present invention can further provide regional and transregional comprehensive emission information which may be shared in a wider range or even worldwide via a cloud platform, thereby helping the supervision department formulate regulatory policies.

According to some embodiments of the present invention, the Traceable emission remote monitoring system and method of the present invention can further provide information such as digital information of the emissions that a single object emits and regional comprehensive emission information to users in need via, for example, a plurality of applications.

According to some embodiments of the present invention, the Traceable emission remote monitoring system and method of the present invention is also particularly convenient for modular design and algorithm update.

It will be comprehended by persons skilled in the art that the features and advantages of the present invention are not limited to the above mentioned. Persons skilled in the art will recognize additional features and advantages of the present invention by reference to the drawings and corresponding detailed description of the present invention. Moreover, a plurality of aspects of a plurality of embodiments may be used, either individually or in any combination, according to expectations and/or requirements.

BRIEF DESCRIPTION OF THE DRAWINGS

The present invention is now described in detail in combination with the drawings in which the same reference numerals represent the same or similar parts, wherein.

DETAILED DESCRIPTION OF THE EMBODIMENTS

Figure 1:
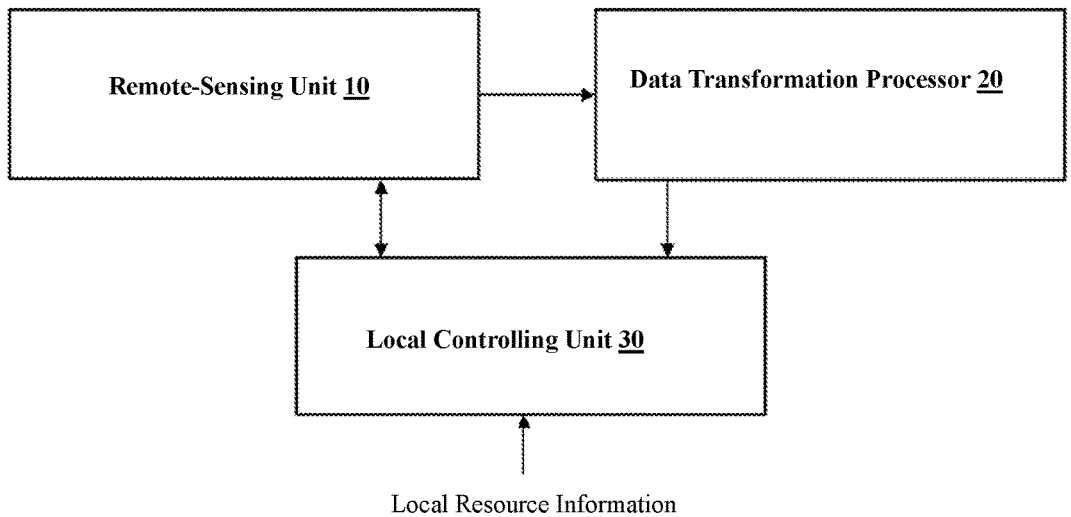
FIG. 1 is a schematic block diagram of a Traceable Emission Remote Monitoring System according to an embodiment of the present invention.

Detailed description of one or more embodiments of the present invention is provided hereinafter together with the drawings illustrating the principle of the present invention. Though the present invention is described in combination with such embodiments, the present invention is not limited to any embodiment. The scope for which protection is sought in the present invention is merely defined by the claims and the present invention may comprise various alternatives, modifications and variations without departing from the spirit and scope of the present invention. Many specific details will be provided in the description hereinafter so as to provide thorough understanding of the present invention. However, persons skilled in the art should understand that these details are provided for illustrative purposes only and the present invention may be implemented in the absence of some or all of these specific details. For the sake of clarity, the technical materials known in the technical field related to the present invention are not described in detail in order to avoid obscuring the present invention unnecessarily.

In addition, when the present invention is elaborated hereinafter in combination with specific embodiments, the system block diagrams and the method flow charts according to the present invention are further provided. However, persons skilled in the art should understand that these block diagrams and flow charts are only for illustration, and for the sake of clarity, only the major modules that are most relevant to the discussion are shown in each of the system block diagrams, the size of each module block does not indicate the actual dimension of the module and/or the dimensional scale relative to other modules, and the position of the module block and the position relative to other module blocks do not indicate the precise position of the module in the actual system and the actual position relative to other modules. Moreover, though the system shown in the embodiments of the present invention comprises a plurality of modules, persons skilled in the art should understand that these modules may be integrated into one or more modules or may be split into more modules as long as the functions of the system in the present invention can be realized. Persons skilled in the art should further understand that, although the information flow directions and/or the connective relations between the modules are indicated by arrows in the system block diagrams for the purpose of illustration only, it means that the information flow directions and/or connective relations may be adjusted as required, rather than that the information flow directions and/or connective relations illustrated as such are unique information flow directions and/or connective relations or that only these illustrated information flow directions and/or connective relations are present. Furthermore, for clarity, some information flow directions and/or connective relations in the embodiments are not explicitly indicated by arrows. Besides, the steps of the method of the present invention are further shown in the context for illustration. However, it should be understood by persons skilled in the art that one or more groups of these steps of the method as shown do not indicate that each of the steps as shown is necessary, nor do they exclude other possible steps or indicate that these steps should be implemented in a given order. Rather, one or some steps may be omitted and/or added according to practical requirements, and the order between the steps may be adjusted according to practical requirements.

In addition, persons skilled in the art should further understand that the terms "connection", "communication connection" or "communicatively connected" or equivalent or similar terms in the context indicate the connective relations that can realize data and/or information transmission established between a system and a terminal and/or other systems, or between modules in a system, or between modules in a system and other systems, devices, modules, terminals and the like outside the system. The connective relations indicated by the terms include wired connection and/or wireless connection, such as connections via 3G, 4G, Wifi or bluetooth communication networks, and other modes that will be developed in the future to realize data and/or information transmission.

The embodiments of the present invention are elaborated in detail hereinafter in combination with the drawings for illustrative purposes only. Persons skilled in the art should understand that the following embodiments are not isolated embodiments, but that one or more embodiments therein may be combined according to requirements without departing from the spirit and scope of the present invention.

Persons skilled in the art should understand that the "traceable" in the context refers to that the emissions that objects (including mobile emission emitting objects and non-mobile emission emitting objects) emit can be traced in time dimension according to the Traceable emission remote monitoring system and method of the present invention, and the emissions that the mobile emission objects emit can be traced in spatial dimension, too. Persons skilled in the art will realize this more deeply after reading the following detailed description.

FIG. 1 is a schematic block diagram of a Traceable Emission Remote Monitoring System 100 according to an embodiment of the present invention. The Traceable Emission Remote Monitoring System 100 comprises a remote sensing unit 10, a transformation data processor 20, and a local control unit 30. Persons skilled in the art should understand that the remote sensing unit 10 corresponds one to one to the transformation data processor 20 in the Traceable Emission Remote Monitoring System provided by the present invention, i.e. each remote sensing unit 10 is connected to one transformation data processor 20, while each of the local control unit 30 may control a plurality of remote sensing units 10 to carry out emission detection of the emitting objects within a certain area (e.g., a plurality of different berths at the same dock, an area including a plurality of oil refineries, power plants, or the like). However, in order to explicitly explain the principle of the present invention, only one remote sensing unit 10 and one transformation data processor 20 are illustrated in the drawings of the context, which is merely for the convenience of stating the principle of the present invention and shall, by no means, be interpreted as limiting the present invention.

The local control unit 30 may dock with a local resource information system (e.g., a local Enterprise Resource Planning (ERP) system) to obtain local resource information. The local resource information system for example may be an information system of a local dock, airport, station, or of a factory such as a power plant, an oil refinery or the like, and the local resource information for example may be information such as a timetable of a mobile object that emits emissions, such as a ship, an aircraft, a vehicle or the like when arriving at and/or departing from a certain berth of a port, an airport or a station, and the model, load, height and the like of the emitting objects, or information such as the emission time of a non-mobile object that emits emissions, e.g., a factory chimney, the production plan of a related production workshop, etc, but is not limited thereto. In the process of operation, the local control unit 30 obtains the desired local resource information first, and then generates control commands according to the local resource information, wherein the control commands, for example, instructing what instructions or instruction sets (i.e., sets of a plurality of instructions) are required to be executed during detection and the order and time for executing the same. The instructions or the instruction sets instruct how to manipulate detection of emissions that the object emits. For example, an instruction of selecting a target gas may indicate detection of sulfur dioxide, detection of nitrogen oxide or simultaneous detection of a plurality of gases; for another example, as for an instruction of adjusting the field of view of a remote sensing means, a preset program may be automatically adjusting the remote sensing device in the remote sensing unit in accordance with the height of the target object that emits the emissions so as to facilitate an operator to further adjust the direction for detection. Instructions may further be, for example, instructions of identifying the objects to be remotely sensed that emit the emissions and instructions of determining the enablement of remote sensing. Persons skilled in the art should understand that various instructions/instruction sets may be integrated into modular integrated instructions, and embedded in the remote sensing unit 10 or the local control unit 30 according to requirements, whereby the control commands can instruct which instruction(s)/instruction set(s) to be invoked, wherein there may be various forms of instructions/instruction sets. For example, the instructions/instruction sets can be fully automatic programs that are programmed and set beforehand, or can be instructions that are programmed and set beforehand but require manual operation, or can be semi-automatic instructions that combine the former.

The local control unit 30 then transmits the control commands to the remote sensing unit 10 for manipulating detection of emissions (e.g., a mixed gas that is emitted) that an object emits. The local control unit 30 may further obtain the updated local resource information periodically so that detection of the emissions that the object emits can be better arranged in the circumstances where the local resource information is altered owing to some reasons, e.g., mobile emission, where the object might depart at a time different from the original timetable (e.g., early or late arrival/departure) owing to some reasons, or information such as the emission time of a non-mobile object that emits emissions (e.g., a factory chimney), or where the production plan of a related production workshop and the like is changed owing to some reasons.

In some embodiments, the remote sensing unit 10 may further transmit feedback information to the local control unit 30. The feedback information can be status feedback information, e.g., whether the remote sensing unit 10 is under detection or in an idle state. The feedback information can also be fault feedback information. For example, as the specified instructions or instruction sets cannot be retrieved owing to errors in the transmission of control commands, the local control unit 30 regenerates new control commands after receiving the fault feedback information, and transmits the new control commands to the remote sensing unit 10 for manipulating detection of the object that emits emissions. The fault feedback information can further be information indicating that the remote sensing device in the remote sensing unit 10 breaks down. The local control unit 30 can instruct restoration or replacement of the remote sensing device after receiving the information. The feedback information can be regular self-check information, or feedback information transmitted depending on intelligent judgment, or temporary feedback information transmitted by human (e.g., a site user at the remote sensing unit 10). The feedback information can be automatically transmitted by the remote sensing unit 10 according to the settings or transmitted by a site user at the remote sensing unit 10, but is not limited thereto.

The remote sensing unit 10 may generally be mounted at, for example, a berth of a dock, an airport or a station, an open space near a factory and/or other places according to practical requirements. When a mobile object that emits emissions and/or other objects to be detected that emit harmful gases and/or greenhouse gases travel into a certain range (e.g., hundreds or even thousands of meters) away from the remote sensing unit 10 or when a non-mobile object that emits emissions (e.g., a chimney of an oil refinery or a power plant) starts to exhaust smoke because, for example, the factory starts production according to the arrangements, the remote sensing unit 10 may invoke corresponding instructions/instruction sets according to the control commands from the local control unit 30, thereby collecting individual emission data concerning the emissions (e.g., the mixed gases as emitted) that an object emits via remote sensing technology. The individual emission data, for example, may be spectrum of the mixed gases that the object emits, but are not limited thereto. In some embodiments, the individual emission data are interference spectra of the mixed gases that the object emits.

The individual emission data collected by the remote sensing unit 10 are then transmitted to the transformation data processor 20 communicatively connected therewith for processing. In some embodiments, the remote sensing unit 10 further preprocesses the individual emission data before transmitting the individual emission data to the transformation data processor 20. In some embodiments, preprocessing is to carry out data compression on the individual emission data. The format in which the data are compressed can be any commonly-used compression format as long as lossless transmission of data can be realized. In some embodiments, principal component analysis is adopted for data compression.

The transformation data processor 20 analyzes the received individual emission data, e.g., through quantitative spectroscopic analysis, thereby obtaining the first analytic result. The first analytic result is a result obtained by analyzing and calculating the individual emission data collected by the transformation data processor 20. The first analytic result is a result obtained by analyzing the data collected on emission behavior within a single emission detection task specified by a individual emitter. For example, in some embodiments, the collected individual emission data is first transformed into transmittance spectra/absorption spectra, and then fitting analysis is performed on the spectral curve of the transformed transmittance spectra/absorption spectra according to the Beer-Lambert Law to obtain the gas content and concentration as the first analytic result. In some embodiments, the first analytic result may include a category of the target gas to be detected in the mixed gases that the object emits and/or the concentration of each target gas to be detected in the mixed gases as emitted. In some embodiments, the first analytic result may further include blackness features of the smoke emitted by the object. In some embodiments, the transformation data processor 20 further buffers the individual emission data received from the remote sensing unit 10 first in order to enhance flexibility, so that it is unnecessary that detection and analysis of the emissions that the object emits should be carried out synchronously. In some embodiments, in order to improve the precision of the first analytic result, the transformation data processor 20 further utilizes auxiliary information when analyzing the individual emission data, the auxiliary information being, for example, the existing spectral library, the distance between the object that emits emissions and the remote sensing unit 10, the ambient temperature, the wind speed, the humidity and the like, but not limited thereto.

The transformation data processor 20 subsequently transmits the obtained first analytic result to the local control unit 30 connected therewith and stores the same in the local control unit 30 for subsequent analysis. In some embodiments, the transformation data processor 20 further transmits and stores the individual emission data received from the remote sensing unit 10 and the auxiliary information utilized when obtaining the first analytic result in the local control unit 30.

The local control unit 30 may further perform other types of derivative analysis to obtain a second analytic result. The second analytic result is a result (also called a new second analytic result) obtained by the local control unit 30 performing derivative analysis and calculation on the first analytic result and/or the second analytic result previously stored in the local control unit 30, which is a derivative analytic result obtained in a certain region (e.g., in a region governed by the local control unit, etc.) as per the service demands. In some embodiments, some other auxiliary information (e.g., one or more of the abovementioned auxiliary information) is further utilized in order to obtain the second analytic result. The obtained second analytic result is also stored in the local control unit 30.

In some embodiments, the local control unit 30 only stores the data (e.g., the first analytic result and the second analytic result, and further comprising the collected individual emission data and auxiliary information, etc. in some embodiments) for a certain period of time. The certain period of time, for example, may be several months, one year or several years. After storage for the certain period of time, the stored data will be overwritten or deleted.

In some embodiments, a local user at the local control unit 30 can further carry out operations directly such as viewing and downloading the data stored therein (e.g., the first analytic result and the second analytic result, and further comprising the collected individual emission data and auxiliary information, etc. in some embodiments).

Figure 2:
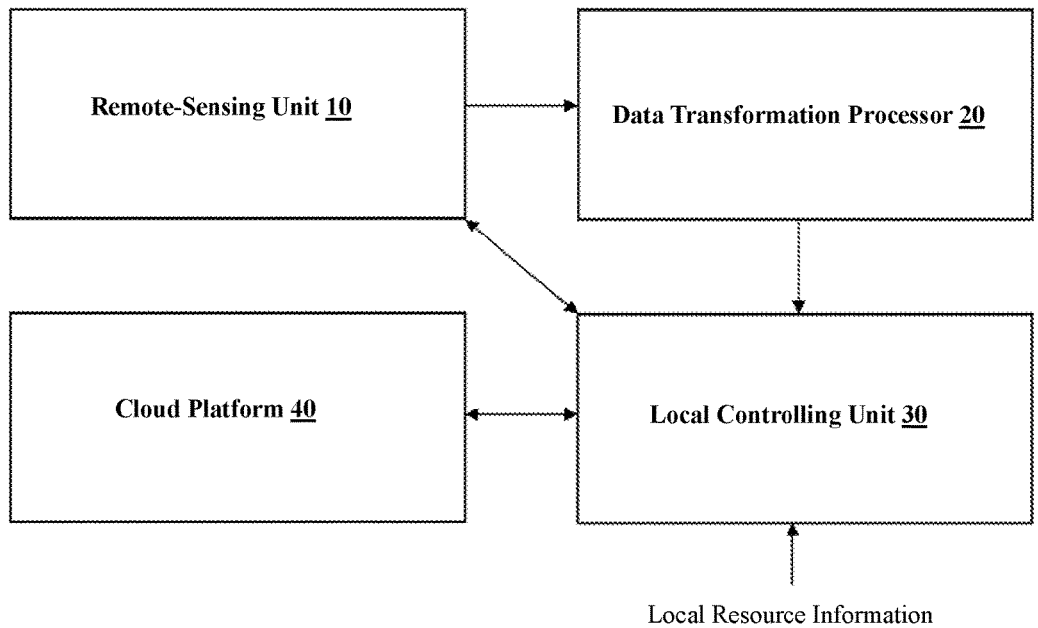
FIG. 2 is a schematic block diagram of a Traceable Emission Remote Monitoring System according to some embodiments of the present invention.

FIG. 2 is a schematic block diagram of a Traceable Emission Remote Monitoring System 100 according to other embodiments of the present invention. As compared with the Traceable Emission Remote Monitoring System 100 in FIG. 1, the Traceable Emission Remote Monitoring System 100 in FIG. 2 further comprises a cloud platform 40 connected to the local control unit 30. The local control unit 30 may upload or synchronize the second analytic result stored therein to the cloud platform 40, thereby enabling the emission data of the object that emits emissions to be shared within a wide range or even globally. In some embodiments, the local control unit 30 also uploads or synchronizes the first analytic result (further comprising the collected individual emission data and auxiliary information, etc. in some embodiments) stored therein to the cloud platform 40 for sharing.

The cloud platform 40 may store the information and data by adopting an appropriate storage mode according to practical requirements. In some embodiments, the cloud platform 40 employs a distributed storage mode to improve speed and accuracy of data access, but it is not limited thereto. Instead, the cloud platform 40 may store the data by employing other storage modes or a storage mode applicable to cloud storage and developed in the future.

The cloud platform 40 can comprehensively analyze the new second analytic result (i.e., the latest second analytic result obtained) and/or all or part of the second analytic result previously stored in the cloud platform 40. The second analytic result utilized during comprehensive analysis is not limited to the second analytic result in a specific region (e.g., a specific region governed by a specific local control unit 30). Rather, the second analytic result concerning the emissions in a plurality of regions or all the regions uploaded or synchronized to the cloud platform 40 may be comprehensively analyzed to obtain a comprehensive analysis report. The comprehensive analysis report is a comprehensive analytic result involving the emissions that an object emits and generated by the cloud platform 40. In some embodiments, the cloud platform 40 may provide comprehensive analysis reports at regular time. For example, a comprehensive analysis is carried out per period of time (e.g., annually) to obtain the comprehensive analytic report, or a single comprehensive analysis report may be provided according to the requirements and/or requests of a specific user. The comprehensive analysis report can be provided to a user in a certain manner. In some embodiments, the comprehensive analysis report is only provided to a user who has paid the fee. For example, a user who has paid the fee may send a request to the cloud platform 40 to customize a specific comprehensive analysis report, or the user who has paid the fee downloads the desired comprehensive analysis report from the cloud platform 40 via authentication (e.g., a password). The user may also be a specific user that satisfies specific requirements and is authorized to customize/view/download the comprehensive analysis report. In some embodiments, the user interacts with the cloud platform 40 via a plurality of Apps connected with the cloud platform 40. The plurality of Apps can be, e.g., mobile applications, web applications and the like, but are not limited thereto.

Each of the modules of the Traceable Emission Remote Monitoring System 100 is presented hereinabove for illustrative purposes only. Persons skilled in the art should understand that the modules can be configured in other manners, e.g., the transformation data processor 20 and the remote sensing unit 10 or the local control unit 30 may be installed separately or may be integrated as long as the functions of the present invention can be realized.

In traditional sampling detection methods, e.g., in the traditional detection of ships at port, a detection device and an analysis device are usually arranged in a stand-alone system, and an inspector is required to operate at the site and can usually detect the emissions that one object emits each time. Thus, it is not only inconvenient and time-consuming, but also requires relatively high manual detection expenses. Moreover, continuous and real-time detection of the emissions that the object emits cannot be realized either. By contrast, the Traceable Emission Remote Monitoring System according to the present invention may realize real-time continuous detection of the emitting objects at a plurality of berths simultaneously via a plurality of remote sensing units controlled by one local control unit. Such non-sampling detection system and method is convenient and efficient, and will not disturb normal operation of the emitting objects at all.

In addition, as for the emissions of chimneys of factories like power plants, oil refineries and so on, the detection mode of traditional environmental sampling cannot accurately measure such emissions for being influenced by factors such as environment, climate, wind direction, wind speed, altitude and the like. The Traceable Emission Remote Monitoring System according to the present invention may simultaneously measure the emissions of a plurality of chimneys in a more accurate manner via a plurality of remote sensing units controlled by one local control unit in the case where various factors mentioned above are taken into account.

Furthermore, for example, as for bunkering ports for ships such as Hong Kong, Singapore and so on, a sufficient amount of a certain type of fuels that conform to the standard are generally supplied to the ships by a supplier currently in accordance with the contract of purchase and sale. However, such conditions often exist as that the supplier substitutes an inferior fuel for a superior fuel or that the ship owner makes a false report that he/she has purchased and used a superior fuel, which actually lead to an increase in pollutant emissions at port. The Traceable Emission Remote Monitoring System according to the present invention may rapidly analyze the individual emission data collected in real time, rapidly determine whether the objects that emit the emissions have changed the fuels, and generate enterprise self-check reports required to be submitted according to the requirements of the supervision department or fill in corresponding data required in the self-check reports. The Traceable Emission Remote Monitoring System is simple, fast, and efficient, and satisfactorily eradicates the existing conditions where the enterprises provide false detection reports.

Besides, as compared with the existing detection systems, the Traceable Emission Remote Monitoring System according to the present invention can further detect the emissions that the objects emit in a more accurate manner. In the prior art, for example, as to the emissions of aircrafts, the total amount of the carbon emissions of a certain category and/or a certain model of aircrafts can normally be estimated only according to the fuel emission efficiency index and fuel consumption, and the actual fuel emission data of a single aircraft will not be detected practically. However, in fact, even for the same model of the aircrafts, different environments such as during cruising, hovering, taking off, landing, ground taxiing, different service lives, different pilots' operational habits and the like would all affect the fuel emission efficiency of the aircrafts' actual fuel emissions. Thus, the traditional estimation mode cannot accurately calculate the emissions of an individual aircraft. On the contrary, the Traceable Emission Remote Monitoring System according to the present invention can readily detect the emissions that each object emits, rather than merely roughly estimate the emissions that a certain category and/or a certain model of objects emit as in the prior art. Moreover, the Traceable emission remote monitoring system and method according to the present invention can further take into account auxiliary information such as ambient temperature, wind speed, humidity and the like, and thereby can analyze the emissions that the objects emit in a more accurate manner.

Moreover, the emissions of factories such as power plants, oil refineries and the like as the upstream emission units of the mobile emitting objects, such as automobiles, steamboats and the like that are driven by fuel or electric power also require to be integrated into the global overall emission detection system. However, the existing technical means cannot provide such kind of overall emission measurement. The Traceable Emission Remote Monitoring System according to the present invention may detect the emissions that a single object emits (e.g., means of transportation and chimneys of factories such as power plants, oil refineries and the like) on an industry chain of energy transportation, thereby analyzing the actual emissions of the entire industry chain in a more accurate manner.

Further, the Traceable Emission Remote Monitoring System according to the present invention can further realize emission digitization of a single object that emits emissions. For example, an emission archive of each object that emits emissions may be established with the aid of the Traceable Emission Remote Monitoring System of the present invention, the emission archive including, for example, an emission history of a single object that emits emissions in a coordinate axis of time, annual emissions of a target gas in a coordinate axis of a certain time (e.g., year), an emission credit record of the object that emits emissions, etc., but not limited thereto. The digital information concerning the emissions that the single object emits may be shared in a wider range or even worldwide via a cloud platform, i.e., sharing can also be realized by using a cloud platform to interface with business systems even in the condition where the business systems do not interface with one another. This will significantly facilitate supervision of the emissions. For example, purposeful supervision and service may be carried out on the single object that emits emissions and different models of emitting objects. For example, penalties such as warning, fines, or forbidding entry into a specific region (e.g., a specific port, city or the like) may be implemented on the emitting objects which are high or have exceeded the standard. For another example, if the emission archives of a majority of ships belonging to a certain type of ships show relatively high emissions of sulfur dioxide, it can be suggested that the sulfur dioxide emissions of this type of ships are relatively heavy as a whole, in turn the causes thereof can be analyzed, for example, whether it is resulted from the design of the type of ships themselves or resulted from the fuel that contains a high sulfur content as used, and thus pertinent regulatory measures can be taken therefor. Meanwhile, the digital emission information of these emitting objects may also provide the manufacturers of the objects that emit the emissions with beneficial reference and guidance.

Moreover, the Traceable Emission Remote Monitoring System according to the present invention can further provide regional and trans-regional comprehensive emission information, such as the total emissions of all ports, airports and/or stations in a certain region as mentioned above, all types of emitting objects, the rankings of the emission effectiveness of all the ports, airports and/or stations, and so on. The regional comprehensive emission information may be shared in a wider range or even worldwide via a cloud platform, thereby helping the supervision department formulate regulatory strategies.

The Traceable Emission Remote Monitoring System according to the present invention can further provide a user in need, e.g., a user who has paid the fee, with information such as the digital information of the emissions that a single object emits and regional and trans-regional comprehensive emission information via, for example, a plurality of applications, thereby satisfying all-round requirements, rather than merely applying the limited emission information as collected to the detection report of the supervision department as the existing detection systems do.

In addition, persons skilled in the art should also understand that the Traceable Emission Remote Monitoring System according to the present invention can be easily updated, adjusted and used owing to a modular design concept. Besides, the Traceable Emission Remote Monitoring System and algorithm according to the present invention has satisfactory compatibility, and the algorithm used for analysis can be easily written into a corresponding module. Moreover, since the individual emission data as originally collected may also be stored, the stored original individual emission data can be conveniently used for analysis with a new algorithm as developed. The new algorithm is used for reanalysis, and the analytic results of each of the algorithms are compared to optimize the algorithms.

These advantages mentioned above will become more obvious in various embodiments of the present invention described hereinafter.

Figure 3:
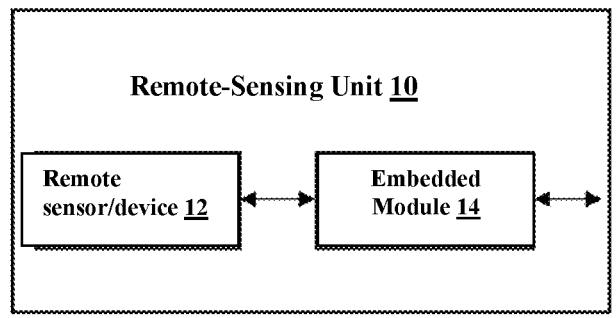
FIG. 3 is a schematic block diagram of an embodiment of a unit of the Traceable Emission Remote Monitoring System according to FIG. 1 or FIG. 2.

FIG. 3 is a schematic block diagram of an embodiment of a remote sensing unit 10 of the Traceable Emission Remote Monitoring System 100 according to FIG. 1 or FIG. 2. The remote sensing unit 10 comprises a remote sensing device 12 and an embedded module 14 connected to the remote sensing device 12. The remote sensing device 12 may be any type of remote sensing device that can detect an object to be detected (e.g., a mixed gas emitted by an object to be detected that emits emissions). In some embodiments, the remote sensing device 12 is a Fourier Transform Infrared Spectrometer. The remote sensing device 12 can also be an Ultraviolet Differential Absorption Spectrum Analyzer, a Tunable Diode Laser Absorption Spectroscopy (TDLAS) or a Differential Absorption Lidar (DIAL). In some other embodiments, the remote sensing device 12 may further comprise a visible light or infrared imaging device. In some further embodiments, the remote sensing device 12 is further combined and/or integrated with a dust blackness detecting instrument, e.g., a blackness detector based on Ringelmann blackness, such as a Ringelmann smoke meter, a Ringelmann smoke telescope, a photoelectric smoke detector or the like, thereby enabling detection of the black smoke that an object emits.

The embedded module 14 can manipulate the detection of emissions that an object emits according to the received control commands. For example, when a mobile object to be detected that emits emissions travels into a certain distance away from the remote sensing device 12 or when a non-mobile object that emits emissions (e.g., a chimney of an oil refinery or a power plant) exhausts because, for example, the factory starts production according to the arrangements, detection of the emissions that these target objects emit is initiated.

The embedded module 14, for example, may be a microcomputer, an application-specific integrated circuit, a microprocessor or any other system. The embedded module 14 may have a human-machine interaction interface and a data interface that performs data interaction with other modules when necessary. The embedded module 14 may further be a system such as a raspberry pi system, a Digital Signal Processor (DSP) system, or a Field Programmable Gate Array (FPGA) system, but not limited thereto.

The remote sensing unit 10 may generally be mounted at a berth of a dock, an airport or a station, or an open space near the chimneys of a factory such as a power plant or an oil refinery and/or other places according to practical requirements. When a ship, an aircraft, a vehicle and/or other mobile objects to be detected that emit harmful gases and/or greenhouse gases travel into a range (e.g., hundreds or even thousands of meters) away from the remote sensing device 12 in the remote sensing unit 10 or when a non-mobile object that emits emissions (e.g., a chimney of an oil refinery or a power plant) exhausts because, for example, the factory starts production according to the arrangements, the remote sensing device 12 may invoke corresponding instructions/instruction sets according to the control commands from the local control unit 30, thereby collecting individual emission data concerning the mixed gases that the object emits via remote sensing technology. The individual emission data, for example, may be spectrum of the mixed gases that the object emits, but are not limited thereto. In some embodiments, the individual emission data are interference spectra of the mixed gases that the object emits.

In some embodiments, the embedded module 14 may further send feedback information to the local control unit 30. The feedback information can be status feedback information, e.g., whether the remote sensing device 12 is under detection or in an idle state. The feedback information can also be fault feedback information. For example, as the specified instructions or instruction sets cannot be retrieved owing to errors in the transmission of control commands, the local control unit 30 regenerates new control commands after receiving the fault feedback information, and transmits the new control commands to the embedded module 14 in the remote sensing unit 10 for manipulating remote sensing of the object that emits emissions. The fault feedback information can further be information indicating that the remote sensing device 12 in the remote sensing unit 10 breaks down, but is not limited thereto. The feedback information can be automatically transmitted by the embedded module 14 according to the settings or transmitted by a site user at the remote sensing unit 10, but is not limited thereto. In one embodiment, when the remote sensing device 12 breaks down, the site user at the remote sensing unit 10 sends the fault information to the local control unit 30 via the embedded module 14 to arrange maintenance or replace the remote sensing device 12. In some embodiments, when the remote sensing device 12 breaks down, the embedded module 14 automatically sends the fault information to the local control unit 30 according to the predefined settings. In some further embodiments, an additional backup remote sensing device is further provided at the same berth. When receiving the fault information from one of the remote sensing means, the local control unit 30 generates and transmits the control commands and activates the backup remote sensing device for remote sensing.

The remote sensing device 12 transmits the collected individual emission data to the embedded module 14 which then continues to transmit the individual emission data to the transformation data processor 20 for processing. In some embodiments, the embedded module 14 further preprocesses the individual emission data before transmitting the individual emission data to the transformation data processor 20. In some embodiments, preprocessing is to carry out data compression on the individual emission data. The format in which the data are compressed can be any commonly-used compression format as long as lossless transmission of data can be realized. In some embodiments, principal component analysis is adopted for data compression.

Figure 4:
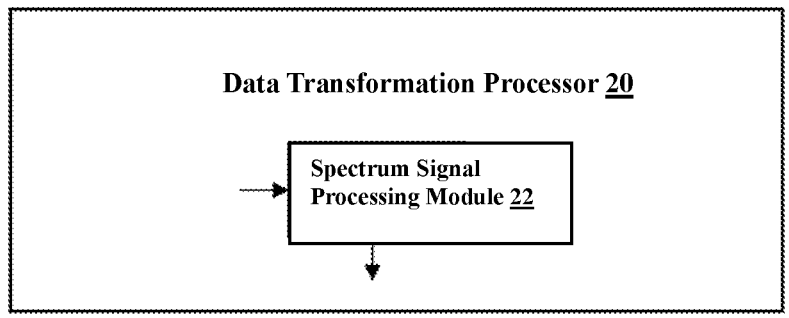
FIG. 4 is a schematic block diagram of an embodiment of a transformation data processor of the Traceable Emission Remote Monitoring System according to FIG. 1 or FIG. 2.

FIG. 4 is a schematic block diagram of an embodiment of a transformation data processor 20 of the Traceable Emission Remote Monitoring System 100 according to FIG. 1 or FIG. 2. The transformation data processor 20 comprises a spectral signal processing module 22. The spectral signal processing module 22 analyzes the received individual emission data to obtain a first analytic result. The first analytic result is a result generated at the terminal of the transformation data processor and, in particular, it is a result obtained by analyzing the data collected on emission behavior within a single emission detection task specified by a particular emission individual. In some embodiments, the spectral signal processing module 22 transforms the received individual emission data into transmittance spectra/absorption spectra first, and then carries out fitting analysis on the spectral curve of the transformed transmittance spectra/absorption spectra according to the Beer-Lambert Law to obtain gas content and concentration as the first analytic result. In some embodiments, the first analytic result may include a category of the target gas to be detected in the mixed gases that the object emits and/or a concentration of each target gas to be detected in the mixed gases emitted. In some embodiments, the first analytic result may further include blackness features of the smoke emitted by the object.

The spectral signal processing module 22 further transmits the obtained first analytic result to the local control unit 30 connected therewith and stores the same therein.

Figure 5:
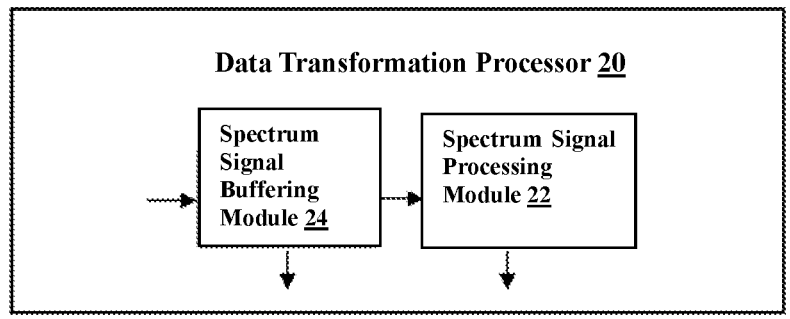
FIG. 5 is a schematic block diagram of another embodiment of a transformation data processor of the Traceable Emission Remote Monitoring System according to FIG. 1 or FIG. 2.

FIG. 5 is a schematic block diagram of another embodiment of a transformation data processor 20 of the Traceable Emission Remote Monitoring System 100 according to FIG. 1 or FIG. 2. As compared with FIG. 4, the transformation data processor 20 according to FIG. 5 further comprises a spectrum signal buffering module 24 connected to the spectral signal processing module 22. The spectrum signal buffering module 24 first receives individual emission data from the remote sensing unit 10 and buffers the individual emission data, so that it is unnecessary that remote sensing and analysis of the emissions that the object emits should be carried out synchronously. The spectrum signal buffering module 22 further transmits the individual emission data to the spectral signal processing module 22 for processing so as to obtain the first analytic result. In some embodiments, the spectrum signal buffering module 22 further transmits the buffered individual emission data to the local control unit 30 and stores the same therein.

Figure 6:
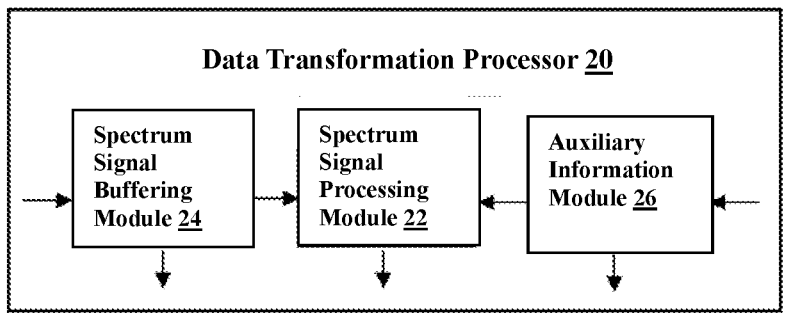
FIG. 6 is a schematic block diagram of a further embodiment of a transformation data processor of the Traceable Emission Remote Monitoring System according to FIG. 1 or FIG. 2.

FIG. 6 is a schematic block diagram of a further embodiment of a transformation data processor 20 of the Traceable Emission Remote Monitoring System 100 according to FIG. 1 or FIG. 2. As compared with FIG. 5, the transformation data processor 20 according to FIG. 6 further comprises an auxiliary information module 26 connected to the spectral signal processing module 22 in addition to the spectral signal processing module 22 and the spectrum signal buffering module 24, so that some auxiliary information can be utilized in the process of deriving the first analytic result to improve the precision of the first analytic result. The auxiliary information, for example, is an existing spectral library, position of an emitting object, ambient temperature, wind speed, humidity or the like, but is not limited thereto. Wherein the spectral library can be a spectral library such as a National Institute of Standards and Technology (NIST) spectral library and/or a High-resolution transmission data base (HITRAN) spectral library, which can be written into the auxiliary information module 26 beforehand and can further be updated by writing in new spectral library information. And the information such as ambient temperature, wind speed, humidity and the like may be obtained by for example arranging a temperature sensor, a wind speed sensor, or a humidity sensor on the remote sensing unit 10 and/or the object that emits emissions. The auxiliary information as obtained may be stored in the auxiliary information module 26 in the transformation data processor 20, and can be transmitted to the spectral signal processing module 22 when the spectral signal processing module 22 is carrying out data analysis, so that the spectral signal processing module 22 may comprehensively analyze the individual emission data along with the auxiliary information to obtain the first analytic result. In some embodiments, the auxiliary information is also transmitted and stored in the local control unit 30.

In one embodiment, in order to obtain a first analytic result, the spectrum of mixed gases emitted by an object that emits emissions is collected by a remote sensing device 12 first, and then background noises are removed. The obtained spectrum with the background noises removed is transformed into a transmittance spectrum, and then fitting is carried out on the transmittance spectrum by means of an NIST spectral library to derive a concentration of carbon monoxide gas to be detected in the mixed gases. In another embodiment, the spectrum of mixed gases emitted by an object that emits emissions is collected by a remote sensing device 12 first, and then background noises are removed. The obtained spectrum with the background noises removed is transformed into an absorption spectrum, and then fitting is carried out on the absorption spectrum by means of an HITRAN spectral library to derive a concentration of carbon monoxide gas to be detected in the mixed gases. In another embodiment, the spectrum of mixed gases emitted by an object that emits emissions is collected first, and after background noises are removed, an absorption spectrum is obtained utilizing envelope curves of background temperature and gas temperature collected on site, and fitting is then carried out to obtain a gas concentration by calculation. In a further embodiment, the spectrum of mixed gases emitted by an object that emits emissions is collected first and is transformed into an absorption spectrum after background noises are removed. After a gas concentration is obtained by fitting (e.g., according to the Beer-Lambert Law or by spectral library fitting), an emission rate of the gas emission source is calculated by a dispersion model method utilizing a wind speed collected on site to obtain a gas concentration. Persons skilled in the art should understand that the spectrum collected by remote sensing can be transformed into an absorption spectrum or a transmittance spectrum by using methods known in the art and/or methods that will be developed in the future. Persons skilled in the art should further understand that these embodiments show the methods and steps of how to utilize individual emission data in combination with auxiliary information to derive a first analytic result for illustrative purposes only, but the methods and steps of deriving the first analytic result are not limited thereto and should comprise other possible methods and steps in which the collected individual emission data can be analyzed and processed. Moreover, the detectable gases are by no means limited to carbon monoxide, but may comprise other target gases to be detected, e.g., such harmful gas as sulfur dioxide and such greenhouse gas as carbon dioxide. Persons skilled in the art should also understand that, in some embodiments, the transformation data processor 20 may only comprise a spectral signal processing module 22 and an auxiliary information module 26, excluding a spectrum signal buffering module 24.

Figure 7:
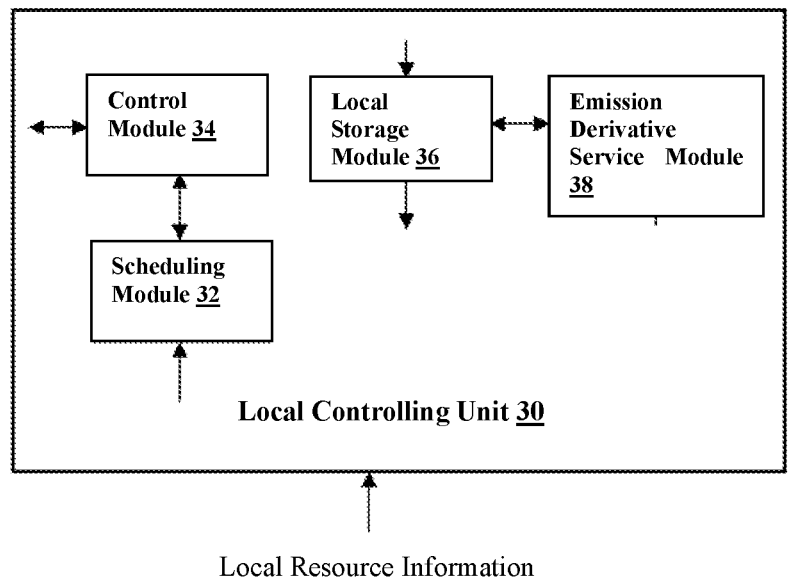
FIG. 7 is a schematic block diagram of an embodiment of a local control unit of the Traceable Emission Remote Monitoring System according to FIG. 1 or FIG. 2.

FIG. 7 is a schematic block diagram of an embodiment of a local control unit 30 of the Traceable Emission Remote Monitoring System 100 according to FIG. 1 or FIG. 2. The local control unit 30 comprises a scheduling module 32 and a control module 34 connected to the scheduling module 32, and a local storage module 36 and an emission derivative service module 38 communicatively connected to the local storage module 36.

During operation, the scheduling module 32 first obtains local resource information from a local resource information system. As previously stated, the local resource information system, for example, may be an information system of a local dock, airport, station or of a factory such as a power plant, an oil refinery or the like, and the local resource information, for example, may be information such as a timetable of a mobile object that emits emissions, such as a ship, an aircraft, a vehicle or the like when arriving at and/or departing from a certain berth of a port, an airport or a station and the model, load, height and the like of the mobile object that emits the emissions, or information such as the emission time of a non-mobile object that emits emissions, e.g., a factory chimney, the production plan of a related production workshop, etc., but is not limited thereto. The scheduling module 32 then transmits the obtained local resource information to the control module 34 which generates control commands according to the local resource information, the control commands, for example, instructing what instructions or instruction sets (i.e., sets of a plurality of instructions) are required to be executed during detection and the order and time for executing the same, e.g., it is stipulated as to when to initiate remote sensing and for which object that emits emissions remote sensing is initiated, the target gas to be sensed remotely, adjustment of the field of view of a remote sensing means, etc. The control module 34 then transmits the generated control commands to an embedded module 14 in the remote sensing unit 10. The embedded module 14 is a module that can manipulate the remote sensing device 12 responsive to the control commands.

The local storage module 36 is used to store the first analytic result. In some embodiments, the local storage module 36 is further used to store the collected individual emission data and the auxiliary information utilized when the first analytic result is obtained.

The local control unit 30 further comprises an emission derivative service module 38 connected to the local storage module 36. The emission derivative service module 38 may further carry out other kinds of derivative analysis to obtain a second analytic result. The second analytic result is a result generated by the local control unit 30 and, in particular, the second analytic result is a result (also called a new second analytic result) obtained by the emission derivative service module 38 in the local control unit 30 performing derivative analysis and calculation on the first analytic result and/or the second analytic result previously stored in the emission derivative service module 38 of the local control unit 30. The second analytic result is a derivative analytic result obtained in a certain region (e.g., in a region governed by the local control unit, etc.) as per the service demands. In some embodiments, some other auxiliary information (e.g., one or more of the abovementioned auxiliary information) is further utilized in order to obtain the second analytic result. The obtained second analytic result is also stored in the local storage module 36.

In some embodiments, the second analytic result comprises whether a mobile object that emits emissions has changed the fuels and when the fuel switch is carried out if the fuels have been changed. For example, the second analytic result can be obtained by further analyzing the first analytic result of the gas emission information of the mobile object that emits emissions (e.g., a vehicle, a ship, an aircraft, or the like). In some embodiments where ships are taken as examples, since the sulfur contents of the fuels as used are different, it can be obtained as to whether a single ship has changed the fuels and when the fuel switch is carried out if the fuels have been changed by analyzing the concentration of sulfur dioxide in the emitted gases. In one embodiment, in order to supervise an oceangoing ship so that the marine high sulfur-containing diesel is replaced with a fuel with a much lower sulfur content as required at the port or dock, the specific process of carrying out derivative analysis on a ship passing through the Hong Kong port utilizing the emission derivative service module 38 is as follows: the concentration of the sulfur dioxide gas emitted by the ship to be detected in the emitted mixed gases within a period of time (e.g., during the time when the ship sails into the port from 1 kilometer away from the port or departs from the port, the ship begins to change the fuel after the ship is berthed at some ports) is analyzed and obtained, and then it is determined as to whether the ship has changed the type of fuel according to the variation of the concentration of sulfur dioxide. If the ship has changed to use a fuel with a much lower sulfur content during a certain period of time, the concentration of sulfur dioxide in the gases it emits will drop sharply. In some embodiments, the emission derivative service module 38 retrieves the historical records of the emission level at which the ship uses different types of fuels in general cases from the data stored in the cloud platform 40, as well as the historical records of the average emission level in the case where the ships with a similar tonnage use different types of fuels, and further compares them with the concentration of sulfur dioxide (i.e., one item of the first analytic results) obtained by the spectral signal processing module 22, thereby determining whether the ship has changed to use the type of fuel with the sulfur content as required by the port and when the replacement has been carried out. In addition, the fuel usage information in the self-check reports of the ships may be further obtained via a local information system, and the concentrations of sulfur dioxide emissions of the ship when different fuels are used can be obtained and retained by comparison as the comparison information for subsequent reexamination, so that the condition of using the fuels can be determined rapidly.

In some embodiments, the second analytic result comprises whether the emissions that a mobile and/or non-mobile object emit(s) have exceeded the black smoke emission standard. This can be derived by comparing the analytic results of the black smoke features detected by the dust blackness detecting instrument incorporated in the remote sensing device 12 with the local black smoke emission standard.

In some embodiments, the second analytic result further comprises the total emissions of the target gas that a specific mobile object emits in a specific region (e.g., a region governed by the local control unit) within a given time (e.g., each year). Persons skilled in the art should understand that the specific mobile object that emits emissions stated herein, for example, may be a specific ship, or may be all the ships belonging to a specific shipping company. For example, in some embodiments, by adding the emissions of a target gas emitted by a specific ship at a specific port (including all the berths of all the docks belonging to the specific port) each time within a year, the emission derivative service module 38 obtains the total emissions of the target gas emitted by the specific ship at the port within the year.

In some embodiments, by analyzing the emissions of the target gas of all the ships entering a specific port (including all the berths of all the docks belonging to the specific port) within a specific time (e.g., within a specific year) may the emission derivative service module 38 obtain the total emissions of the target gas at the port within the specific time.

In some embodiments, the second analytic result further comprises the emissions of the target gas along the time within a specific region (e.g., a region governed by a local control unit). For example, in some embodiments, the second analytic result further comprises a curve of yearly sulfur dioxide emissions of all the ships entering the Hong Kong port.

Persons skilled in the art should understand that the target gas stated in the context can be one or more of the mixed gases (e.g., harmful gases and/or greenhouse gases) that a mobile object emits. The emission derivative service module 38 can analyze and calculate the total annual emissions of a specific target gas (e.g., sulfur dioxide) in the mixed gases, or the total annual emissions of more than one specific target gas (e.g., sulfur dioxide together with carbon monoxide) in the mixed gases. Persons skilled in the art should also understand that the embodiments in which ships are taken as examples in the context may be applied to the conditions such as automobiles, trains and/or aircrafts based on the same or similar principle.

In some embodiments, the second analytic result may further comprise enterprise self-check reports required to be submitted according to the requirements of the supervision department or corresponding data required to be filled in the self-check reports based on the fuel switch conditions of a mobile object that emits emissions. In some embodiments, the emission derivative service module 38 generates enterprise self-check reports required to be submitted according to the requirements of the supervision department or corresponding data required to be filled in the self-check reports according to the fuel switch conditions when each of the ships berths at a port. In some embodiments, such reports should be additionally customized according to different local requirements. In some embodiments, part of the contents of the reports can be directly generated, e.g., when to change the fuel, the new type of fuel, the berthing time, etc., and the other part of the contents of the reports irrelevant to the emissions can be completed manually. In some further embodiments, the self-check reports can be filled in manually according to the analytic result of the emission derivative service module 38.

In some embodiments, the second analytic result may further comprise a regional emission report for environmental decision making by the supervision department. For example, the emission derivative service module 38 may regularly (e.g., each year) generate a regulatory emission report for environmental decision making by the supervision department. In some embodiments, the emission derivative service module 38 can generate a regulatory emission report on the basis of the emissions that an object emits and the fuel switch conditions, the regulatory emission report for example including a ranking of the emissions of the ships arriving at the port and an emission record of a single ship and an emission blacklist, thereby providing reliable decision support for the law enforcement on the ships.

In some embodiments, the second analytic result may further comprise the total annual emissions of a specific target gas (e.g., sulfur dioxide or carbon dioxide) from all the chimneys of a factory such as a thermal power plant or an oil refinery, or may analyze and calculate the total annual emissions of more than one specific target gas (e.g., sulfur dioxide together with carbon monoxide) in the mixed gases.

In some embodiments, the second analytic result further comprises the emissions of the target gas from all the chimneys of one or more factories (e.g., a thermal power plant, and an oil refinery) within a specific region in a coordinate axis of time. For example, in some embodiments, the second analytic result further comprises a curve of yearly sulfur dioxide emissions of the factories in a specific region (e.g., Longgang District, Shenzhen) in a specific city.

In some embodiments, the emission derivative service module 38 can also derive the emissions of the factory per unit product by analyzing the products (e.g., energy output) as generated and the emissions of the corresponding harmful gases and/or the greenhouse gases. Supposing that the factory has introduced a new emission reduction technology or management method, the efficacy of actual emission reduction can be achieved by further analyzing the emissions per unit product.

In some embodiments, the second analytic result further comprises emission archives of each of the emitting objects. For example, in some embodiments, the emission derivative service module 38 creates emission archives for each of the emitting objects in a specific region by analyzing the historical records and data (e.g., the second analytic result previously stored therein) of, for example, each of the emitting objects (e.g., mobile emitting objects such as ships, automobiles, trains, aircrafts, etc. and non-mobile emitting objects such as chimneys) stored therein. The emission archives, for example, may comprise emission credit records (e.g., times of emission that exceeds the standard, and times of penalties owing to emissions that exceed the standard) of each of the objects that emit missions in a coordinate axis of time (e.g., in a unit of year), emission trend maps of the emitting objects (e.g., curves of the emissions that the mobile objects emit each time when entering the port/station (e.g., the total annual emissions divided by the times of entering the port/station), and emission trend graphs of the non-mobile emitting objects per unit time (e.g., in a unit of year)), etc., thereby supervising and servicing all the emitting objects and/or the companies, organizations or groups to which the objects belong with pertinence. Persons skilled in the art should understand that the emission archives are only described illustratively hereinabove, and the contents of the emission archives are not limited thereto and can be extended or modified according to practical requirements.

The embodiments of the second analytic result are provided hereinabove for illustrative purposes only. Persons skilled in the art should understand that all the analytic results obtained by analyzing the first analytic result of the emitting objects and/or the second analytic result previously stored in the local control unit 30 and other auxiliary information (e.g., the historical data of the emissions all the objects emit (including all different regions) that can be retrieved from the cloud platform 40 when necessary) in some cases fall into the scope covered by the second analytic result. For example, the second analytic result may further be a ranking of the emissions at all the docks of the port, etc.

The obtained second analytic result is stored in the local storage module 36.

In some embodiments, the local storage module 36 can further upload or synchronize the second analytic result stored therein to the cloud platform 40. In some embodiments, the local storage module 36 also uploads the first analytic result (further comprising the collected individual emission data and auxiliary information, etc. in some embodiments) stored therein to the cloud platform 40.

In some embodiments, the local storage module 36 in the local control unit 30 only stores the data (e.g., the first analytic result and the second analytic result, and further comprising the collected individual emission data and auxiliary information, etc. in some embodiments) for a certain period of time. The certain period of time, for example, can be several months, one year or several years. After storage for the certain period of time, the stored data will be overwritten or deleted.

In some embodiments, a local user at the local control unit 30 can further carry out operations directly such as viewing and downloading the data (e.g., the first analytic result and the second analytic result, and further comprising the collected individual emission data and auxiliary information, etc. in some embodiments) stored in the local storage module 36.

Figure 8:
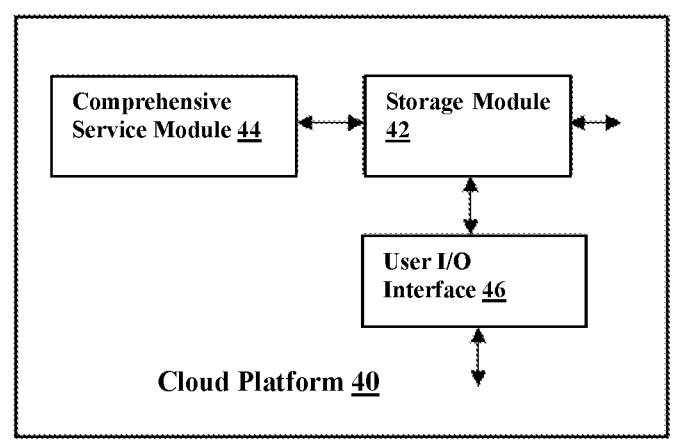
FIG. 8 is a schematic block diagram of an embodiment of a cloud platform of the Traceable Emission Remote Monitoring System according to FIG. 2.

FIG. 8 is a schematic block diagram of an embodiment of a cloud platform 40 of the Traceable Emission Remote Monitoring System 100 according to FIG. 2. The cloud platform 40 comprises a storage module 42, a comprehensive service module 44 communicatively connected to the storage module 42 and a user input/output (I/O) interface 46 communicatively connected to the storage module 42.

The cloud platform 40 can receive the second analytic result from the local control unit 30. In some embodiments, the cloud platform 40 can also receive the first analytic result (further comprising the collected individual emission data and auxiliary information, etc. in some embodiments) from the local control unit 30 and store the same in the storage module 42. The storage module 42 may store the information and data by adopting an appropriate storage mode according to practical requirements. In some embodiments, the storage module 42 employs a distributed storage mode to improve speed and accuracy of data access. In some embodiments, the storage module 42 employs a Hadoop Distributed File System (HDFS). The data are stored in a plurality of servers, and a data group is established by one data node corresponding to a plurality of data nodes, so that the capacity of rapidly reading data fault tolerance can be improved. Storage and invoke instructions or programs will be divided into many parts, each part can be executed or re-executed on any node of a cluster, and the interaction therebetween across the servers may also base on a specific protocol of TCP/IP, whereby the universality of communication is guaranteed. Persons skilled in the art should comprehend that the storage mode is not limited thereto and, instead, the data may be stored by employing other storage modes or a storage mode applicable to cloud storage and developed in the future.

The cloud platform 40 can also comprehensively analyze the new second analytic result (i.e., the latest second analytic result obtained) and/or all or part of the second analytic result previously stored in the cloud platform 40. The second analytic result utilized during comprehensive analysis is not limited to the second analytic result in a specific region (e.g., a specific region governed by a specific local control unit 30). Rather, the second analytic result concerning the emissions in a plurality of regions or all the regions uploaded or synchronized to the cloud platform 40 may be comprehensively analyzed to obtain a comprehensive analysis report. The comprehensive analysis report is a comprehensive analytic result involving the emissions that an object emits and generated by the cloud platform 40.

Persons skilled in the art should note that, since the cloud platform 40 can receive data (e.g., the second analytic result) from each of the local control units 30 and comprehensively analyze the data, the obtained comprehensive analysis report mainly covers all kinds of cross-time and trans-regional analytic results.

In some embodiments, the comprehensive analysis report comprises a comprehensive emission archive of a single mobile object that emits emissions. For example, the cloud platform 40 may synthesize the emission archives of all the mobile emitting objects from all the different local control units 30, thereby establishing comprehensive emission archives for all the single mobile emitting objects. For example, by comprehensively analyzing the times of emission that exceeds the standard and the times of penalties owing to emissions that exceed the standard of a specific mobile object that emits emissions in each region, and the emission trend map of the specific mobile object that emits emissions each time when entering the port/station or the like in each region, the cloud platform 40 establishes the emission credit records of the specific mobile object that emits emissions, e.g., across the province, nationwide or even worldwide. The cloud platform 40 may further directly integrate the emission archives concerning the non-mobile emitting objects received from each of the local control units 30 into the comprehensive analysis reports as the comprehensive emission archives of the non-mobile emitting objects in each region. Persons skilled in the art should understand that the emission archives are only described illustratively hereinabove, and the contents of the emission archives are not limited thereto and can be extended or modified according to practical requirements.

In some embodiments, the comprehensive analysis report may further comprise the emissions of the greenhouse gases and/or harmful gases that an object emits per unit production process in the coordinate axis of time (e.g., in a unit of year). In some embodiments, the comprehensive service module 44 analyzes the emissions that a certain object emits within a given time in the past to obtain the emissions of the greenhouse gases and/or harmful gases it emits per unit production process in the period of time. For example, the gas emissions of a ship loaded with containers when handling a container at the port, or the gas emissions of a dry bulk carrier when handling a ton of freight at the port may indicate the emissions of the greenhouse gases and/or harmful gases that the object emits per unit production process in the production process.

In some embodiments, the comprehensive analysis report may further comprise an emission footprint of freight. An emission footprint during transportation, for example, refers to a collection process of greenhouse and/or harmful gas emissions caused by the activity of freight transportation. In some embodiments, the comprehensive service module 44 detects the emissions of a list of freight during the entire transportation from the manufacturing enterprise to the end users to obtain the emission footprint during transportation of the list, or an overall emission footprint of a list of freight from manufacturing to reaching the end users.

In some embodiments, the comprehensive analysis report comprises the total emissions (e.g., total annual emissions) of all the ports, airports, stations, or all kinds of factories or the like in a region (e.g., a specific province) within a given period of time (e.g., a year). In some embodiments, the comprehensive service module 44 analyzes the emissions of the target gas in a region, e.g., each of the ports, stations or airports of a province in the past year, to obtain the total emissions of the target gas in the province within the period of time. As the ports, airports, stations and the like are all required to submit respective emission inventories regularly to the departments concerned (e.g., the International Maritime Organization, the International Civil Aviation Organization, etc.), wherein the emissions from self-operation and emissions that the objects emit are comprised. The current emission inventories are inaccurate since calculation is carried out only based on the number of emitting objects and the berthing time as the parameters. However, the comprehensive analysis report derived from comprehensive analysis by the comprehensive service module 44 has satisfactorily solved the existing problem.

In some embodiments, the comprehensive analysis report may further comprise all types of emitting objects, the transportation enterprises and the rankings of the emission effectiveness of each of the ports, airports and stations, etc. The emission effectiveness refers to the average emissions of the greenhouse gases and/or harmful gases of the mobile emitting objects, the transportation enterprises and all transportation junctions per unit production process within a given time. In some embodiments, the comprehensive service module 44 derives the rankings of the average emission effectiveness of all types of emitting objects at each of the transportation junctions in a period of time in the past by analyzing the emission effectiveness of all types of emitting objects in the period of time in the past. For example, an average gas emission of a container ship when handling a container in the process of berthing at a port in a year. In some embodiments, the comprehensive service module 44 derives the rankings of the emission effectiveness of a transportation enterprise by analyzing and comparing the emission conditions of all the emitting objects subordinate to the transportation enterprise in a period of time in the past. In some embodiments, by analyzing and comprising the emissions of each of the ports, stations or airports in a period of time in the past, the comprehensive service module 44 derives the rankings of the emission effectiveness of each of the ports, stations or airports in the period of time, such as the rankings of emissions for handling per unit container as derived based on the throughput and the total emissions of the container port, or the rankings of emissions of the transportation junctions when generating economic income per unit currency.

Likewise, in some embodiments, the comprehensive analysis report may further comprise the rankings of the emission effectiveness of each of the non-mobile emitting objects, such as a power plant and an oil refinery. For example, the emission effectiveness of each oil refinery is ranked according to the sulfur dioxide emissions as generated by the production of per unit diesel.

The embodiments of the comprehensive analysis report as presented above are for illustrative purposes only. Persons skilled in the art should understand that various analyses may be made according to practical requirements based on the emission data (e.g., the second analytic result, etc.) of each object that emits emissions in each region shared on the cloud platform 40 so as to satisfy the requirements of different users. All the analytic results that can be obtained based on the shared emission data fall into the scope covered by the comprehensive analysis report.

The comprehensive analysis report is stored in the storage module 42. In some embodiments, the cloud platform 40 may provide a regular comprehensive analysis report. For example, a comprehensive analysis is made every half a year or every year to obtain a comprehensive analysis report. In some embodiments, the cloud platform 40 provides a single comprehensive analysis report according to the requirements and/or requests of a specific user. The comprehensive analysis report can be provided to the user in a certain manner. In some embodiments, the comprehensive analysis report is only provided to a user who has paid the fee. For example, the user who has paid the fee may send a request to the cloud platform 40 via a user I/O interface 46 through a plurality of applications to customize a comprehensive analysis report, the plurality of applications, for example, being mobile applications, web applications and the like, but not limited thereto. In some embodiments, the cloud platform 40 sends the corresponding analysis report to the user who has paid the fee responsive to the request, or the user who has paid the fee may be authorized to download the requested comprehensive analysis report.

Figure 9:
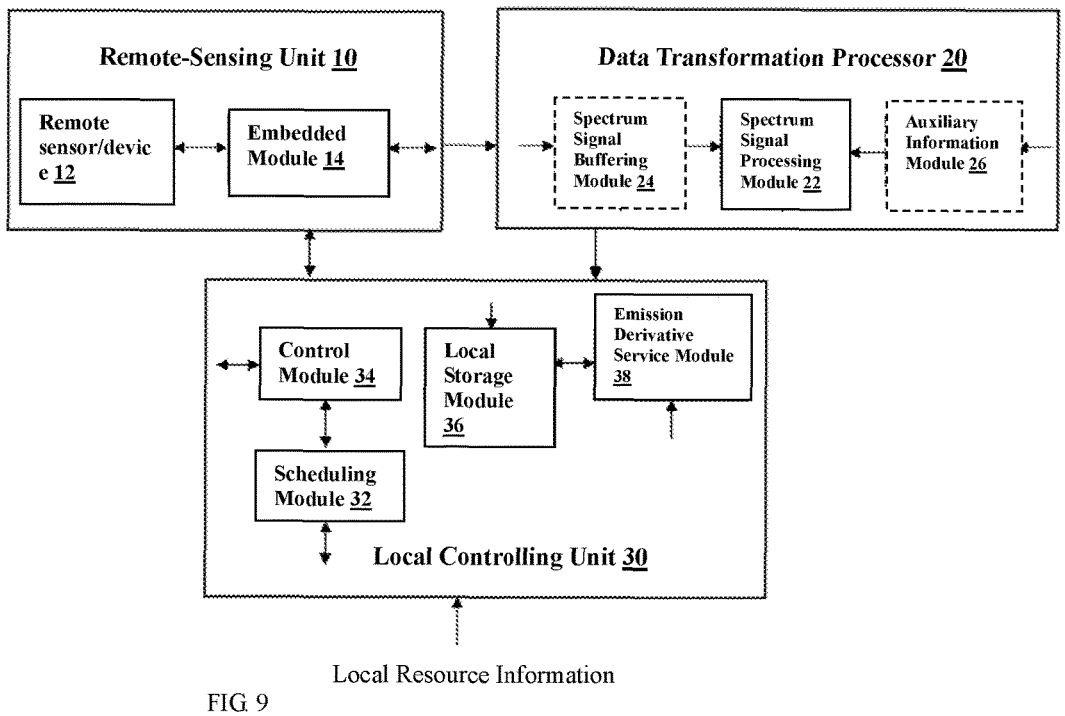
FIG. 9 is a more detailed schematic block diagram of an embodiment of the Traceable Emission Remote Monitoring System according to FIG. 1.

FIG. 9 is a more detailed schematic block diagram of an embodiment of the Traceable Emission Remote Monitoring System 100 according to FIG. 1. The Traceable Emission Remote Monitoring System 100 comprises a remote sensing unit 10 according to FIG. 3, a transformation data processor 20 according to FIG. 4 or FIG. 5 or FIG. 6, a local control unit 30 according to FIG. 7 and a cloud platform 40 according to FIG. 8. Therein, the remote sensing unit 10, for example, may comprise a remote sensing device 12 and an embedded module 14 communicatively connected to the remote sensing device 12 as illustrated in FIG. 3. The transformation data processor 20 may, as illustrated in FIG. 4, only comprise a spectral signal processing module 22, or may, as illustrated in FIG. 5, comprise a spectral signal processing module 22 and a spectrum signal buffering module 24 connected thereto, or may, as illustrated in FIG. 6, comprise a spectral signal processing module 22, a spectrum signal buffering module 24 and an auxiliary information module 26. The local control unit 30 may, as illustrated in FIG. 7, comprise a scheduling module 32 and a control module 34 communicatively connected to the scheduling module 32, and a local storage module 36 and an emission derivative service module 38 communicatively connected to the local storage module 36. The cloud platform 40 may, as illustrated in FIG. 8, comprises a storage module 42, a comprehensive service module 44 connected to the storage module 42 and a user I/O interface 46 connected to the storage module 42.

During operation, local resource information is first obtained from a local resource information system by a scheduling module 32 in a local control unit 30. As stated above, the local resource information system, for example, may be an information system of a local dock, airport, station or a factory, and the local resource information, for example, may be information such as a timetable of mobile emitting objects, such as ships, aircrafts, vehicles or the like when arriving at and/or departing from a certain berth of a port, an airport or a station and their models, loads, heights and the like, or information such as the emission time of non-mobile emitting objects, e.g., factory chimneys, the production plan of related production workshops, etc., but is not limited thereto. The scheduling module 32 then transmits the obtained local resource information to the control module 34 which generates corresponding control commands according to the local resource information, the control commands, for example, instructing what instructions or instruction sets (i.e., sets of a plurality of instructions) are required to be executed during detection and the order and time for executing the same. The control module 34 then transmits the generated control commands to an embedded module 14 in the remote sensing unit 10, wherein the embedded module 14, for example, is an embedded module 14 as described with reference to FIG. 3.

In some embodiments, an on-site user at the remote sensing unit 10 can further transmit feedback information to the control module 34 in the local control unit 30 via the embedded module 14. The feedback information can be status feedback information, e.g., whether the remote sensing device 12 is under detection or in an idle state. The feedback information can also be fault feedback information. For example, as the specified instructions or instruction sets cannot be retrieved owing to errors in the transmission of control commands, the control module 34 in the local control unit 30 regenerates new control commands after receiving the fault feedback information, and transmits the control commands to the embedded module 14 in the remote sensing unit 10 for manipulating detection of the emissions that an object emits. The fault feedback information can further be information indicating that the remote sensing device 12 in the remote sensing unit 10 breaks down, but is not limited thereto. The feedback information can be automatically transmitted by the embedded module 14 according to the settings or transmitted by a site user at the remote sensing unit 10, but is not limited thereto. In one embodiment, when the remote sensing device 12 breaks down, the site user at the remote sensing unit 10 transmits the fault information to the local control unit 30 via the embedded module 14 to arrange maintenance or replacement of the remote sensing device 12. In another embodiment, when the remote sensing device 12 breaks down, the embedded module 14 automatically sends the fault information to the control module 34 in the local control unit 30 according to the predefined settings. In some other embodiments, an additional backup remote sensing device is further provided at the same berth. When receiving the fault information from one of the remote sensing means, the control module 34 in the local control unit 30 generates and transmits the control commands and activates the backup remote sensing device for remote sensing.

The remote sensing device 12, for example, is the remote sensing device 12 with reference to FIG. 3. The remote sensing device 12 may generally be mounted at a berth of a port or a dock, an airport or a station, an open space near a factory and/or other places according to practical requirements. When a ship, an aircraft, a vehicle and/or other mobile objects to be detected that emit harmful gases and/or greenhouse gases travel into a range (e.g., hundreds or even thousands of meters) away from the remote sensing device 12 or when a non-mobile object that emits emissions (e.g., a chimney of an oil refinery or a power plant) starts to exhaust smoke because, for example, the factory starts production according to the arrangements, the remote sensing device 12 may invoke corresponding instructions/instruction sets according to the control commands from the control module 34 in the local control unit 30, thereby collecting individual emission data concerning the emissions (e.g., the mixed gases) that the objects emit via remote sensing technology. The individual emission data, for example, may be spectrum of the mixed gases that the objects emit, but are not limited thereto. In some embodiments, the individual emission data are interference spectra of the mixed gases that the objects emit.

The remote sensing device 12 transmits the collected individual emission data to the embedded module 14 which then continues to transmit the individual emission data to the transformation data processor 20 for processing. In some embodiments, the embedded module 14 further preprocesses the individual emission data before transmitting the individual emission data to the transformation data processor 20. In some embodiments, preprocessing is to carry out data compression on the individual emission data. The format in which the data are compressed can be any commonly-used compression format as long as lossless transmission of data can be realized. In some embodiments, principal component analysis is adopted for data compression.

The spectral signal processing module 22 in the transformation data processor 20 analyzes the received individual emission data to obtain a first analytic result. The first analytic result is a result generated at the terminal of the transformation data processor and, in particular, it is a result obtained by data collection and analysis on the emission behavior within a single emission detection task specified by a particular emission individual.

In some embodiments, the transformation data processor 20 may, as illustrated in FIG. 5, comprise a spectrum signal buffering module 24. The spectrum signal buffering module 24 first receives individual emission data from the remote sensing unit 10 and buffers the individual emission data, so that it is unnecessary that remote sensing and analysis of the emissions that an object emits should be carried out synchronously. The spectrum signal buffering module 22 further transmits the individual emission data to the spectral signal processing module 22 for processing to obtain a first analytic result. In some embodiments, the spectrum signal buffering module 22 further transmits the buffered individual emission data to the local control unit 30 and stores the same therein.

In some further embodiments, the transformation data processor 20 may, as illustrated in FIG. 6, comprise an auxiliary information module 26 connected to the spectral signal processing module 22 so that some auxiliary information can be utilized in the process of deriving the first analytic result to improve the precision of the first analytic result. The description about the auxiliary information, for example, may be as stated above with reference to FIG. 6.

The first analytic result for example may comprise a category of the target gas to be detected in the mixed gases that an object emits and/or a concentration of each target gas to be detected in the emitted mixed gases. In some embodiments, the first analytic result may further comprise blackness features of the smoke emitted by the object. The description about the first analytic result and how to obtain the first analytic result may be as stated above with reference to FIGS. 4-6.

The local control unit 30 further comprises a local storage module 36 and an emission derivative service module 38 connected thereto in addition to a scheduling module 32 and a control module 34. The emission derivative service module 38 may further carry out other kinds of derivative analysis to obtain a second analytic result. The second analytic result is a result generated by the local control unit 30 and, in particular, the second analytic result is a result (also called a new second analytic result) obtained by the emission derivative service module 38 in the local control unit 30 performing derivative analysis and calculation on the first analytic result and/or the second analytic result previously stored in the emission derivative service module 38 of the local control unit 30. The second analytic result is a derivative analytic result obtained in a certain region (e.g., in a region governed by the local control unit, etc.) as per the service demands. The description about the second analytic result and how to obtain the second analytic result, for example, may be as stated above with reference to FIG. 7.

In some embodiments, the local storage module 36 in the local control unit 30 only stores the data (e.g., the first analytic result and the second analytic result, and further comprising the collected individual emission data and auxiliary information, etc. in some embodiments) for a certain period of time. The certain period of time, for example, can be several months, one year or several years. After storage for the certain period of time, the stored data will be overwritten or deleted.

In some embodiments, a local user at the local control unit 30 can further carry out operations directly such as viewing and downloading the data (e.g., the first analytic result and the second analytic result, and further comprising the collected individual emission data and auxiliary information, etc. in some embodiments) stored in the local storage module 36.

Figure 10:
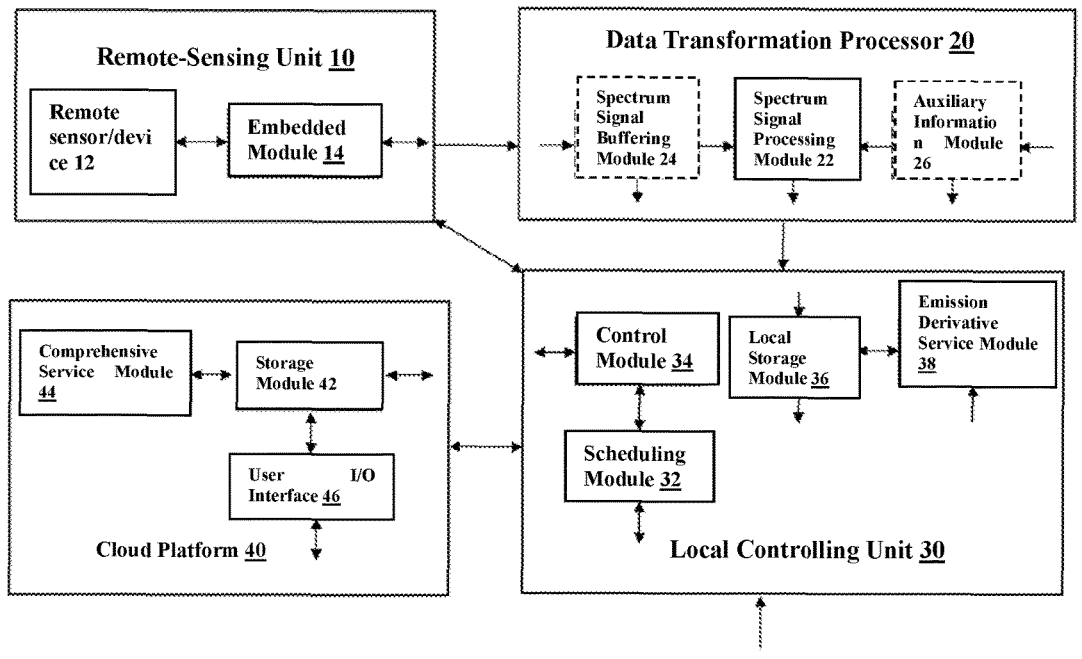
FIG. 10 is a more detailed schematic block diagram of an embodiment of the Traceable Emission Remote Monitoring System according to FIG. 2.

FIG. 10 is a more detailed schematic block diagram of an embodiment of the Traceable Emission Remote Monitoring System 100 according to FIG. 2. As illustrated in FIG. 2, the Traceable Emission Remote Monitoring System 100 further comprises a cloud platform 40. The cloud platform 40 for example may, as illustrated in FIG. 8, comprise a storage module 42, a comprehensive service module 44 communicatively connected to the storage module 42 and a user input/output (I/O) interface 46 communicatively connected to the storage module 42. The cloud platform 40 can receive a second analytic result from a local control unit 30. In some embodiments, the cloud platform 40 can also receive a first analytic result (further comprising the collected individual emission data and auxiliary information and the like in some embodiments) from the local control unit 30 and store the same in the storage module 42. The storage module 42 for example may be as stated above with reference to FIG. 8.

The cloud platform 40 may further comprehensively analyze the second analytic result concerning the emissions of a plurality of regions or all the regions uploaded or synchronized to the cloud platform 40 to obtain a comprehensive analysis report. The comprehensive analysis report is a comprehensive analytic result involving the emissions that an object emits and generated by the cloud platform 40. The comprehensive analysis report may be, for example, as stated above with reference to FIG. 8.

The comprehensive analysis report may be stored in the storage module 42. In some embodiments, the cloud platform 40 may provide a regular comprehensive analysis report. For example, a comprehensive analysis is made every half a year or every year to obtain a comprehensive analysis report. In some embodiments, the cloud platform 40 provides a single comprehensive analysis report according to the requirements and/or requests of a specific user. The comprehensive analysis report can be provided to the user in a certain manner. In some embodiments, the comprehensive analysis report is only provided to a user who has paid the fee. For example, the user who has paid the fee may send a request to the cloud platform 40 via a user I/O interface 46 through a plurality of applications to customize a comprehensive analysis report, the plurality of applications being, for example, mobile applications, web applications and the like, but not limited thereto. In some embodiments, the cloud platform 40 sends the corresponding analysis report to the user who has paid the fee responsive to the request, or the user who has paid the fee may be authorized to download the requested comprehensive analysis report.

Figure 11:
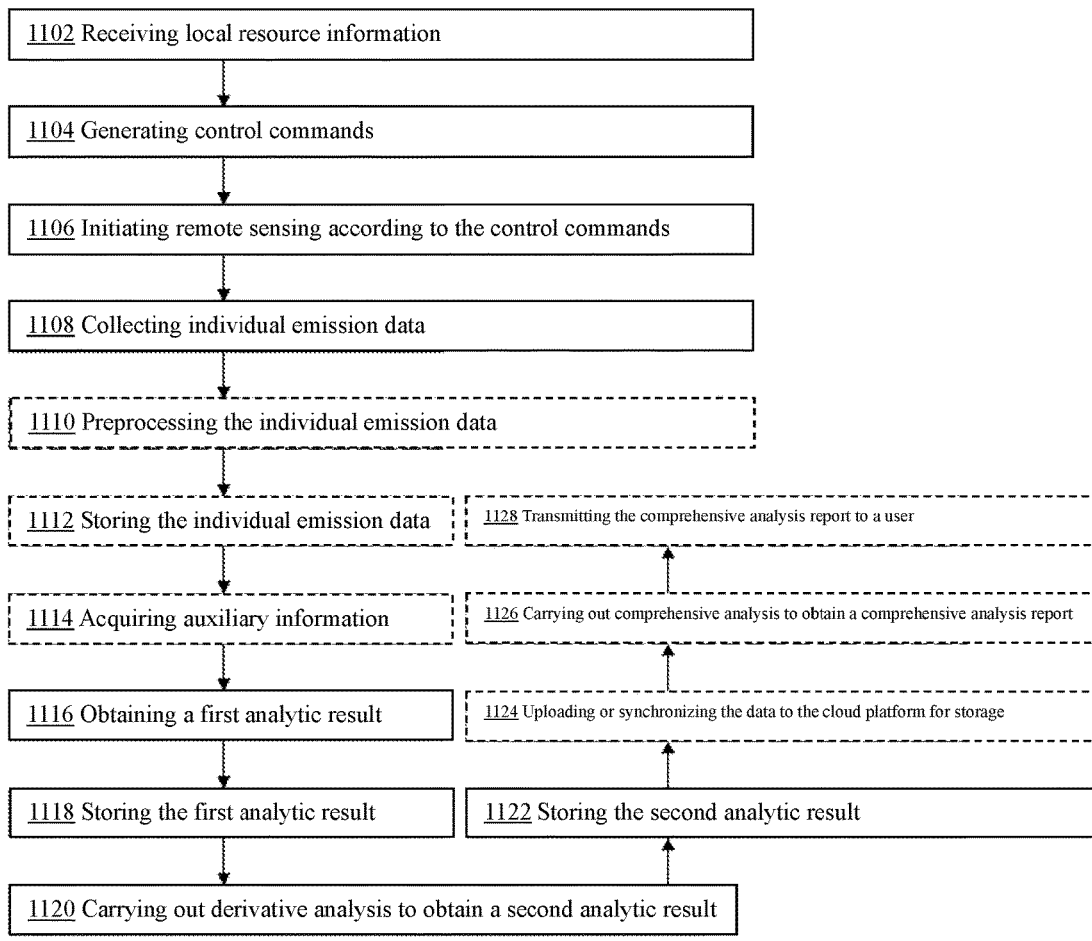
FIG. 11 is a schematic flow chart of a traceable emission remote sensing method according to an embodiment of the present invention.

In addition, the Applicant should comprehend that, in the Traceable Emission Remote Monitoring System 100 in FIG. 9 and FIG. 10, the dashed blocks indicate that the modules are not necessary, but may be present according to the requirements in some embodiments.

FIG. 11 is a schematic flow chart 1100 of a traceable emission remote sensing method according to an embodiment of the present invention, the method for example being a method that can be executed by the Traceable Emission Remote Monitoring System 100 according to FIGS. 1-10.

In step 1102, local resource information is received. For example, as previously stated, the local resource information is received from a local resource system by a scheduling module 32 in a local control unit 30. As stated previously, the local resource information system, for example, may be an information system of a local dock, airport, station, or of a factory such as a power plant, an oil refinery or the like, and the local resource information, for example, may be information such as a timetable of a mobile object that emits emissions, such as a ship, an aircraft, a vehicle or the like when arriving at and/or departing from a certain berth of a port, an airport or a station and the model, load, height and the like of the object that emits the emissions, or information such as the emission time of a non-mobile object that emits emissions, e.g., a factory chimney, the production plan of a related production workshop, etc., but is not limited thereto.

In step 1104, control commands are generated according to the received local resource information. For example, as stated previously, the scheduling module 32 transmits the obtained local resource information to the control module 34 which generates corresponding control commands according to the local resource information, the control commands, for example, instructing what instructions or instruction sets are required to be executed during detection and the order and time for executing the same, e.g., it is stipulated as to when to initiate remote sensing and for which object that emits emissions the remote sensing is initiated, the target gas, adjustment of the field of view of a remote sensing means, etc., but not limited thereto. In some embodiments, the control commands instruct what instructions or instruction sets to be invoked and the order and time for executing the instructions.

In step 1106, remote sensing is initiated according to the control commands. For example, as previously stated, the control module 34 then transmits the generated control commands to the embedded module 14 in the remote sensing unit 10, the embedded module 14 initiating the remote sensing of the emissions that an object emits according to the control commands. In some embodiments, the instructed instructions/instruction sets are invoked according to the control commands, and remote sensing of a specific object that emits emissions is initiated in a specified time. The remote sensing unit 10 may generally be mounted at a berth of a port or a dock, an airport or a station, an open space near a factory chimney and/or other places according to practical requirements. When a ship, an aircraft, a vehicle and/or other objects to be detected that emit harmful gases and/or greenhouse gases travel into a certain range (e.g., hundreds or even thousands of meters) away from the remote sensing unit or when a non-mobile object that emits emissions (e.g., a chimney of an oil refinery or a power plant) starts to exhaust smoke because, for example, the factory starts production according to the arrangements, the remote sensing device 12 in the remote sensing unit 10 initiates remote sensing of the object that emits emissions according to the instructions of the control commands. The remote sensing unit 10 and the process of remote sensing may be as stated above with reference to FIGS. 1-3.

In step 1108, individual emission data are collected. For example, as previously stated, the remote sensing device 12 collects the individual emission data of an object that emits emissions via remote sensing technology. The individual emission data for example may be spectrum of the emissions (e.g., mixed gases) that the object emits, but are not limited thereto. For example, in some embodiments, the individual emission data are interference spectra of the mixed gases that the object emits.

In step 1110, the collected individual emission data are preprocessed. For example, as stated previously, the embedded module 14 further preprocesses the individual emission data before transmitting the individual emission data to the transformation data processor 20. In some embodiments, preprocessing is to carry out data compression on the individual emission data. The format in which the data are compressed can be any commonly-used compression format as long as lossless transmission of data can be realized. In some embodiments, principal component analysis is adopted for data compression.

In step 1112, individual emission data are stored. For example, as stated previously, the individual emission data are stored in the local control unit 30. In some embodiments, the individual emission data are further buffered in the transformation data processor 20 so that it is unnecessary that detection and analysis of the emissions that the object emits should be carried out synchronously.

In step 1114, auxiliary information is obtained. For example, as stated previously, an auxiliary information module 26 in the transformation data processor 20 is utilized to store auxiliary information. The auxiliary information for example is the existing spectral library, the distance between the object that emits emissions and the remote sensing means, the ambient temperature, the wind speed, the humidity and the like, but is not limited thereto. Therein, the spectral library can be a spectral library such as an NIST spectral library and/or an HITRAN spectral library. However, the information such as the ambient temperature, wind speed, humidity and the like may be obtained in real time by arranging a temperature sensor, a wind speed sensor, or a humidity sensor. The auxiliary information as obtained may be stored in the auxiliary information module in the transformation data processor 20, and can be transmitted to the spectral signal processing module 22 when the spectral signal processing module 22 is carrying out data analysis, so that the spectral signal processing module 22 may analyze the individual emission data along with the auxiliary information to obtain the first analytic result. By utilizing the auxiliary information can the analytic precision of gas concentration and the like in the mixed gases that an individual emits be improved.

In step 1116, a first analytic result is obtained. For example, as stated previously, the first analytic result and the obtainment of the first analytic result may be, for example, as stated above with reference to FIG. 3 or FIG. 4 or FIG. 7.

In step 1118, the first analytic result is stored. For example, as previously stated, the first analytic result is transmitted to the local control unit 30 and stored therein.

In step 1120, derivative analysis is made to obtain a second analytic result. For example, as previously stated, the second analytic result and the obtainment of the second analytic result may be, for example, as stated above with reference to FIG. 5 or FIG. 7.

In step 1124, the second analytic result is stored in the local control unit.

In step 1122, data are transmitted to the cloud platform for storage. In some embodiments, the data are new second analytic results obtained in the local control unit 30. In some embodiments, the data may further comprise the originally collected individual emission data, the first analytic result and auxiliary information, etc. The storage of data by the cloud platform may be, for example, as sated above with reference to FIG. 7.

In step 1126, emission data are comprehensively analyzed in the cloud platform to obtain a comprehensive analysis report. The comprehensive analysis and the comprehensive analysis report may be, for example, as stated above with reference to FIG. 8.

In step 1128, the comprehensive analysis report is transmitted to a user. For example, as stated previously, the comprehensive analysis report can be provided to a user in a certain manner. For example, the comprehensive analysis report can be only provided to a user who has paid the fee. For example, the user who has paid the fee sends a request to the cloud platform 40 to customize a comprehensive analysis report, or the user who has paid the fee downloads the desired comprehensive analysis report from the cloud platform 40 via authentication (e.g., a password). In some embodiments, the user interacts with the cloud platform 40 via a plurality of applications connected to the cloud platform 40. The plurality of applications can be, e.g., mobile applications, web applications and the like, but are not limited thereto.

Persons skilled in the art should comprehend that the abovementioned steps are only for illustrative purposes, and do not include all the steps. For example, in some embodiments, the remote sensing unit further sends feedback information to the local control unit. The feedback information can be status feedback information (such as information of the remote sensing unit per se: whether it is under detection or in an idle state; information concerning that the instructions are executed normally and environmental information: whether there is a detectable target while no control commands are received, or whether the target to be detected does not appear, or whether the weather is unfavorable to detection, etc.), or fault feedback information (for example, as the specified instructions or instruction sets cannot be retrieved owing to errors in the transmission of control commands, or the remote sensing device breaks down). The local control unit generates corresponding control commands after receiving the feedback information, and transmits the control commands to the remote sensing unit for manipulating detection of the object that emits emissions. In some embodiments, the local control unit first collects from the remote sensing unit status information of the remote sensing unit, e.g., whether the remote sensing unit can operate normally, before sending the control commands to the remote sensing unit. If the collected status information shows that the remote sensing device in the remote sensing unit breaks down, corresponding processes, such as restoration or replacement, are instructed first.

Persons skilled in the art should also comprehend that the steps shown in FIG. 11 do not indicate that each of the steps comprised is necessary. For example, in some embodiments, before transmitting the individual emission data collected by the remote sensing device 12 to the transformation data processor 20, it is not required to preprocess the same. In some embodiments, the transformation data processor 20 does not use auxiliary information, but directly processes the individual emission data instead to obtain the first analytic result. In some embodiments, it is not required to buffer the individual emission data from the remote sensing unit 10, but the spectral signal processing module 22 receives the individual emission data directly and processes the same to obtain the first analytic result. The dashed blocks in FIG. 11 show the unnecessary steps which may be implemented according to practical requirements.

Persons skilled in the art should further comprehend that the steps shown in FIG. 11 do not indicate that the steps should be implemented strictly according to the order as shown, but that necessary adjustment can be made according to practical requirements.

Though a plurality of embodiments have been described in the text, persons skilled in the art should understand that these embodiments described are all illustrative but not restrictive. Having read the above description of the present invention, persons skilled in the art may conceive of other embodiments of the present invention. For example, necessary modifications and adjustments such as replacement, addition, deletion, integration, division and the like are made to the system and method of the present invention, and all of these modifications and variations fall within the scope of the present invention.

The invention claimed is:

1. A traceable emission remote monitoring system, characterized in that, the system comprises:
   a remote sensing unit for manipulating remote sensing of emissions that an object emits and collecting emission data of an individual emitter via remote sensing technology;
   a transformation data processor connected to the remote sensing unit, for receiving the individual emission data and analyzing the individual emission data to obtain a first analytic result; and
   a local control unit connected to the remote sensing unit and the transformation data processor respectively for:
      receiving local resource information and generating control commands for manipulating the remote sensing of emissions that the object emits based on the local resource information; and
      receiving the first analytic result from the transformation data processor, and analyzing the first analytic result and/or a second analytic result previously stored in the local control unit to obtain a new second analytic result, and storing the new second analytic result.

2. The traceable emission remote monitoring system according to claim 1, characterized in that, the system further comprises:
   a cloud platform connected to the local control unit, the cloud platform being used for:
      receiving and storing the new second analytic result from the local control unit; and
      comprehensively analyzing the new second analytic result and/or all or part of the second analytic result previously stored in the cloud platform to obtain a comprehensive analysis report.

3. The traceable emission remote monitoring system according to claim 1, characterized in that, the remote sensing unit comprises:
   a remote sensing device for collecting individual emission data of the object that emits emissions via remote sensing technology; and
   an embedded module connected to the remote sensing device, the embedded module being used for:
      receiving from the local control unit control commands for manipulating the remote sensing of the emissions that the object emits and manipulating the remote sensing of the emissions that the object emits based on the control commands; and receiving the individual emission data from the remote sensing device, and transmitting the individual emission data to the transformation data processor for processing.

4. The traceable emission remote monitoring system according to claim 1, characterized in that, the transformation data processor comprises:
a spectral signal processing module for analyzing the individual emission data to obtain a first analytic result.

5. The traceable emission remote monitoring system according to claim 1, characterized in that, the local control unit comprises:
a scheduling module for receiving local resource information;
a control module connected to the scheduling module, for receiving local resource information from the scheduling module, and generating the control commands for manipulating the remote sensing of emissions that an object emits based on the local resource information;
an emission derivative service module for analyzing the first analytic result and/or the second analytic result previously stored in the local control unit to obtain the new second analytic result; and
a local storage module for receiving and storing the first analytic result from the transformation data processor and receiving and storing the new second analytic result from the emission derivative service module.

6. The traceable emission remote monitoring system according to claim 2, characterized in that, the cloud platform comprises:
a storage module for receiving and storing the new second analytic result from the local control unit;
a comprehensive service module for comprehensively analyzing the new second analytic result and/or all or part of the second analytic result previously stored in the storage module to obtain a comprehensive analysis report, wherein the obtained comprehensive analysis report is stored in the storage module; and
a user I/O interface for allowing a user to interact with the cloud platform via the user I/O interface.

7. The traceable emission remote monitoring system according to claim 4, characterized in that, the transformation data processor further comprises:
a spectrum signal buffering module connected to the spectral signal processing module, for receiving the individual emission data as collected from the remote sensing unit, and buffering the individual emission data and transmitting the same to the spectral signal processing module for processing.

8. The traceable emission remote monitoring system according to claim 4, characterized in that, the transformation data processor further comprises:
an auxiliary information module connected to the spectral signal processing module for storing auxiliary information which comprises one or more of an existing spectral library, position of an emitting object, ambient temperature, wind speed and humidity, and the spectral signal processing module analyzes the individual emission data in combination with the auxiliary information to obtain a first analytic result.

9. The traceable emission remote monitoring system according to claim 1, characterized in that,
the remote sensing unit is further used for transmitting feedback information to the local control unit; and
the local control unit is further used for responding to the feedback information,
wherein the feedback information comprises one or both of status feedback information and fault feedback information of the remote sensing unit, and the responding comprises the local control unit generating new control commands according to the feedback information, and transmitting the new control commands to the remote sensing unit to instruct manipulation of the remote sensing of emissions that the object emits.

10. The traceable emission remote monitoring system according to claim 1, characterized in that, the individual emission data are transmitted and stored in the local control unit, and the individual emission data and the first analytic result are further uploaded or synchronized to the cloud platform and stored therein.

11. A traceable emission remote sensing method, characterized in that, the method comprises:
receiving local resource information, and generating control commands for manipulating the remote sensing of emissions that an object emits based on the local resource information;
initiating the remote sensing of the emissions that the object emits according to the control commands to collect individual emission data;
analyzing the individual emission data to obtain a first analytic result, and transmitting the first analytic result to a local control unit; and
analyzing the first analytic result and/or a second analytic result previously stored in the local control unit to obtain a new second analytic result and storing the new second analytic result in the local control unit.

12. The traceable emission remote sensing method according to claim 11, characterized in that, the method further comprises:
uploading or synchronizing the new second analytic result to a cloud platform and storing the same in the cloud platform; and
comprehensively analyzing the new second analytic result and/or all or part of the second analytic result previously stored in the cloud platform to obtain a comprehensive analysis report.

13. The traceable emission remote sensing method according to claim 11, characterized in that, the method further comprises:
transmitting feedback information to the local control unit; and
the local control unit responding to the feedback information,
wherein the feedback information comprises one or both of status feedback information and fault feedback information of the remote sensing unit, and the responding comprises the local control unit generating new control commands according to the feedback information, and transmitting the new control commands to the remote sensing unit to instruct manipulation of the remote sensing of emissions that the object emits.

14. The traceable emission remote sensing method according to claim 11, characterized in that, the method further comprises:
analyzing the individual emission data in combination with auxiliary information to obtain the first analytic result, wherein the auxiliary information comprises one or more of a spectral library, position of an emitting object, ambient temperature, wind speed and humidity.

15. The traceable emission remote sensing method according to claim 11, characterized in that, the method further comprises:

buffering the individual emission data prior to analyzing the same.

16. The traceable emission remote sensing method according to claim 12, characterized in that, the method further comprises:
transmitting and storing the individual emission data in a local control unit, and
uploading or synchronizing the individual emission data and the first analytic result to a cloud platform and storing the same therein.

* * * * *